US008623647B2

(12) United States Patent
Tebbi

(10) Patent No.: US 8,623,647 B2
(45) Date of Patent: Jan. 7, 2014

(54) METHODS OF INDUCING LEUKEMIA AND LYMPHOMAS AND DETECTING SUSCEPTIBILITY TO LEUKEMIA/LYMPHOMA

(71) Applicant: Cameron K. Tebbi, Tampa, FL (US)

(72) Inventor: Cameron K. Tebbi, Tampa, FL (US)

( * ) Notice: Subject to any disclaimer, the term of this patent is extended or adjusted under 35 U.S.C. 154(b) by 0 days.

(21) Appl. No.: 13/673,301

(22) Filed: Nov. 9, 2012

(65) Prior Publication Data

US 2013/0137175 A1 May 30, 2013

Related U.S. Application Data

(62) Division of application No. 12/973,153, filed on Dec. 20, 2010.

(51) Int. Cl.
*C12N 5/00* (2006.01)
*C12N 5/0786* (2010.01)

(52) U.S. Cl.
USPC .......................................... 435/375; 435/377

(58) Field of Classification Search
USPC .......................................... 435/7.1, 375, 377
See application file for complete search history.

*Primary Examiner* — Michele K Joike
*Assistant Examiner* — Antonio Galisteo Gonzalez
(74) *Attorney, Agent, or Firm* — Robert J. Varkonyi; Smith & Hopen, P.A.

(57) ABSTRACT

A method is described using *Aspergillus flavus* fungal cultures, EBV or their combination to induce leukemic cell surface markers in mononuclear cells of former or current acute lymphoblastic leukemia/lymphoma patients. Detection of the leukemic transformation by methods known in the art identified patients who have or had acute lymphoblastic leukemia/lymphoma. Unlike aflatoxins, which indiscriminately induce leukemic transformation, the compositions used were specific to acute lymphoblastic leukemia/lymphoma-predisposed patients, but not other cancers or normal controls. An ELISA technique using the described fungal products or EBV and combination can detect individuals with history of leukemia and not controls. The combination of cultures of EBV and *Aspergillus flavus*, with and without radiation, results in the development of a new protein peak. These findings have implications for the etiology of leukemias and lymphomas.

3 Claims, 30 Drawing Sheets

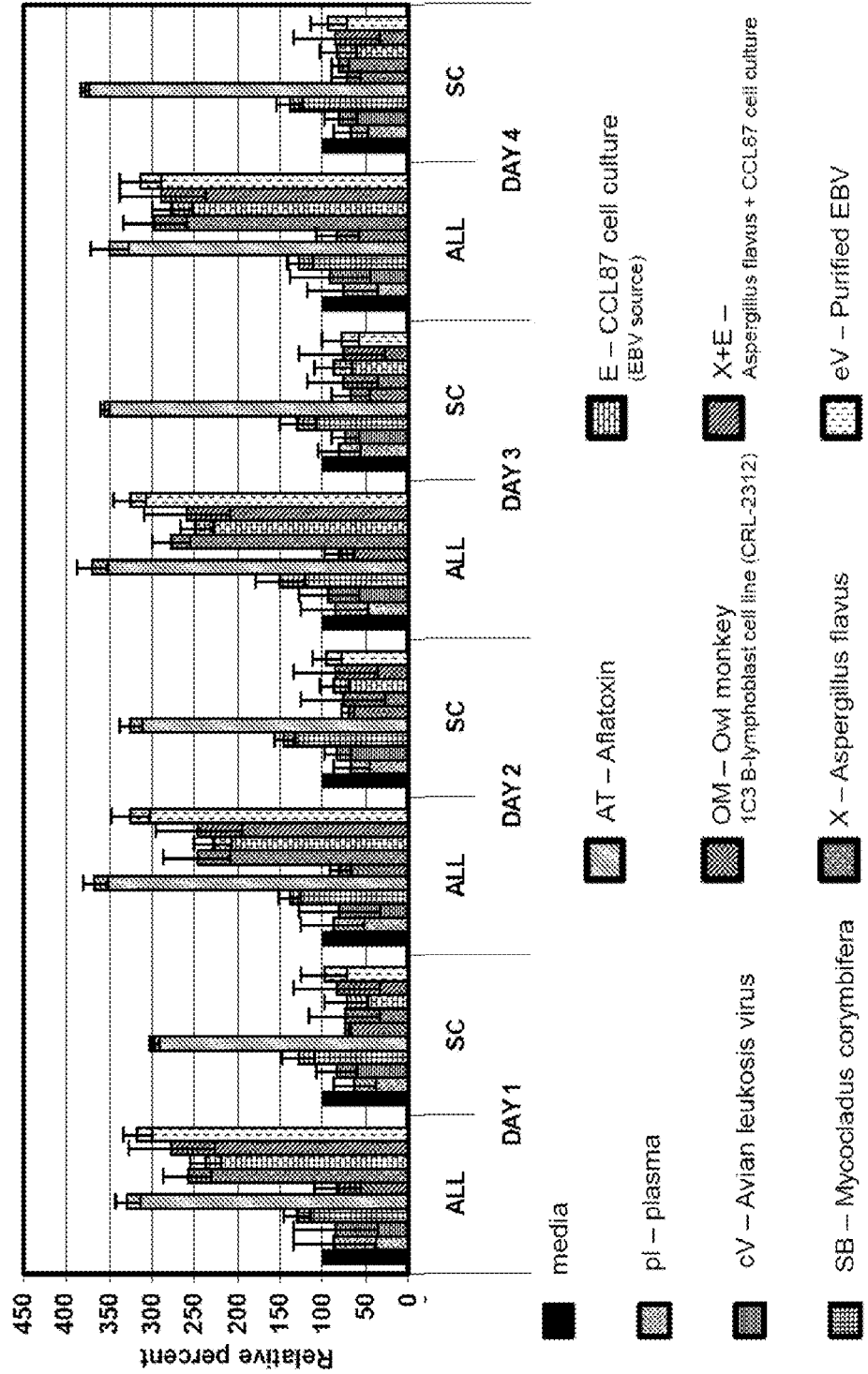

METHODS OF INDUCING LEUKEMIA AND LYMPHOMAS AND DETECTING SUSCEPTIBILITY TO LEUKEMIA/LYMPHOMA

CROSS REFERENCE TO RELATED APPLICATIONS

This application is a divisional application of prior-filed U.S. Nonprovisional patent application Ser. No. 12/973,153, filed Dec. 20, 2010, entitled "Methods of Detecting Susceptibility to Leukemia/Lymphoma and Induction of Leukemia and Lymphomas", the contents of which are hereby incorporated by reference.

FIELD OF INVENTION

This invention relates to medical diagnostics, for use in diseases such as leukemia and diffuse lymphomas and the in vitro re-induction of leukemia in mononuclear leukocyte cells from patients in remission. Specifically, the invention involves a procedure for inducing leukemic or leukemia-like cell surface markers in mononuclear leukocytes and a plasma test for identification and diagnosis of individuals at-risk for leukemia/diffuse lymphomas.

BACKGROUND OF THE INVENTION

Leukemias are a heterogeneous group of cancers of the blood forming organs characterized by production of abnormal leukocytes, their release to circulation and infiltration of organs. The U.S. National Cancer Institute estimates that there were 43,050 new cases in 2010 and 21,840 leukemia-related deaths. Where leukemias can occur at any age, about 90% of cases are diagnosed in adults. By far, the cause of leukemia in the majority of cases is unknown (Itakura H, Coutre S E: Acute lymphoblastic leukemia in adults. In: Greer J P, et al., editors. Leukemia in adults. Philadelphia: Lippincott Williams and Wilkins. 2009. p. 1820; Faderel S, et al., Acute lymphoblastic leukemia. In: Hong W K, et al., editors. Holland-Frei cancer medicine. Eighth Edition, Shelton, Conn.: People's Medical Publishing House, 2010. p. 1591; MacArthur A C, et al., Risk of Childhood Leukemia Associated with Vaccination, Infection, and Medication Use in Childhood. Am J Epidemiol. 2008; 167 (5):598-606). Some of the suggested causes include natural and artificial ionizing radiation (Maloney W. Leukemia in survivors of atomic bombing. N Eng J. Med. 1955; 253:88; Preston D, Kusumi S, Tomonaga M, et al. Cancer incidence in atomic bomb survivors. Part III. Leukemia, lymphoma and myeloma, 1950-1987. Radiat Res. 1994; 137:S68-S97; Little M P, et al., The statistical power of epidemiological studies analyzing the relationship between exposure to ionizing radiation and cancer, with special reference to childhood leukemia and natural background radiation. Radiat Res. 2010; 174 (3):387-402; Davies A, Modan B, Djaldetti M, et al. Epidemiological observations on leukemia in Israel. Arch Intern Med. 1961; 108 (1): 86-90), viruses such as Epstein-Barr Virus (Tokunaga M, et al., Epstein-Barr virus in adult T-cell leukemia/lymphoma. Am J Pathol. 1993; 143 (5): 1263-1268), Human T-lymphotropic virus (HTLV-1) (Phillips A A, et al., A critical analysis of prognostic factors in North American patients with human T-cell lymphotropic virus type-1-associated adult T-cell leukemia/lymphoma: a multicenter clinicopathologic experience and new prognostic score. Cancer. 2010; 116 (14):3438-3446; Jeang K T. HTLV-1 and adult T-cell leukemia: insights into viral transformation of cells 30 years after virus discovery. J Formos Med. Assoc. 2010; 109 (10): 688-93), infections (Greaves M F, Alexander F E. An infectious etiology for common acute lymphoblastic leukemia in childhood? Leukemia. 1993; 7:349-360; Smith M A, et al., Investigation of leukemia cells from children with common acute lymphoblastic leukemia for genomic sequences of the primate polyomaviruses, JC virus, BK virus and simian virus 40. Med Pediatr Oncol. 1999; 33:441-443; Smith M A, et al., Evidence that childhood acute lymphoblastic leukemia is associated with an infectious agent linked to hygiene conditions. Cancer Causes Control. 1998; 9:285-298), some chemicals such as benzene and alkylating chemotherapy agents (Wen W Q, et al., Paternal military service and risk for childhood leukemia in offspring. Am J Epidemiol. 2000; 151:231-240; Momota H, et al., Acute lymphoblastic leukemia after temozolomide treatment for anaplastic astrocytoma in a child with a germline TP53 mutation. Pediatr Blood Cancer. 2010; 55 (3):577-9; Borgmann A, et al., Secondary malignant neoplasms after intensive treatment of relapsed acute lymphoblastic leukaemia in childhood. ALL-REZ BFM Study Group. Eur J Cancer. 2008; 44 (2):257-68), familial predisposition (Karakas Z, Tugcu D, Unuvar A, Atay D, Akcay A, Gedik H, Kayserili H, Dogan O, Anak S, Devecioglu O. Li-Fraumeni syndrome in a Turkish family. Pediatr Hematol Oncol. 2010; (4):197-305; Buffer P A, et al., Environmental and genetic risk factors for childhood leukemia: Appraising the evidence. Cancer Investigation. 2005; 23 (1): 60-75), medications (Tebbi C K, et al., Dexrazoxane-associated risk for acute myeloid leukemia/myelodysplastic syndrome and other secondary malignancies in pediatric Hodgkin's disease. J Clin Oncol. 2007; 25 (5):493-500), genetic factors, chromosomal and metabolic abnormalities (Fong C T, Brodeur G M. Down's syndrome and leukemia: epidemiology, genetics, cytogenetics and mechanisms of leukemogenesis. Cancer Genet Cytogenet. 1987; 28 (1): 55-76; Chao M M, et al., T-cell acute lymphoblastic leukemia in association with Borjeson-Forssman-Lehman syndrome due to a mutation in PHF6. Pediatr Blood Cancer. 2010; 55 (4): 722-4; Kato K, et al., Late recurrence of precursor B-cell acute lymphoblastic leukemia 9 years and 7 months after allogenic hematopoietic stem cell transplantation. J Pediatr Hematol Oncol. 2010; 32 (7):e290-3; Smith M T, et al., Low NAD(P)H: quinine oxidoreductase 1 activity is associated with increased risk of acute leukemia in adults. Blood. 2001; 97:1422-1426; Hengstler J G, et al., Polymorphisms of N-acetyltransferases, glutathione S-transferases, microsomal epoxide hydrolase and sulfotransferases: influence on cancer susceptibility. Recent Results Cancer Res. 1998; 154:47-85; Schenk T M, et al., Multilineage involvement of Philadelphia chromosome positive acute lymphoblastic leukemia. Leukemia. 1998; 12:666-674; Felix C A, et al, Immunoglobulin and T cell receptor gene configuration in acute lymphoblastic leukemia of infancy. Blood. 1987; 70:536-541), immune disorders (Vajdic C M, et al., Are antibody deficiency disorders associated with a narrower range of cancers than other forms of immunodeficiency? Blood. 2010; 116 (8):1228-34), and environmental issues (Magnani C, et al., Parental occupation and other environmental factors in the etiology of leukemias and non-Hodgkin's lymphomas in childhood: a case-control study. Tumori. 1990; 76 (5):413-9; Non-Ionizing Radiation, Part 1: Static and Extremely Low-Frequency (ELF) Electric and Magnetic Fields (IARC Monographs on the Evaluation of the Carcinogenic Risks). Geneva: World Health Organization. pp. 332-333, 338, 2002; Kroll M E, et al., Childhood cancer and magnetic fields from high-voltage lines in England and Wales: a case-control study. Br J Cancer. 2010; 103 (7):1122-7; Little, M P, et al., The statistical power of epidemiological studies analyzing the relationship between exposure to ionizing radiation and cancer, with special reference to childhood leukemia and natural background radiation. Radiat Res 2010; 174 (3):387-402). None of the above factors can be consistently applied to a majority of cases, nor have they been definitely proven to predictably induce leukemia in all exposed individuals.

Leukemias may be subdivided into groups, including acute and chronic leukemia. In acute leukemia, there is a rapid increase in immature white blood cells (leukocytes) formed in the bone marrow and a reduction in production of normal blood cells. Acute leukemias include acute lymphoblastic leukemias (ALL) and acute myelogenous leukemias (AML). Chronic leukemias include chronic lymphocytic and myelogenous leukemia (CLL and CML). Due to the rapid progression and accumulation of the malignant cells in acute leukemias, immediate treatment is required.

Acute leukemias are the most common forms of cancer in children. Acute lymphoblastic leukemia (ALL) and diffuse lymphomas constitute a significant portion of cancers in childhood. ALL is the most frequent leukemia in the pediatric population (Pui C H. Acute lymphoblastic leukemia in children. Curr opin oncol. 2000; 12:3-12) accounting for a quarter of all childhood cancers and approximately 75% of all leukemias in children, with peak incidence of two to five years of age (Pui C H. Acute lymphoblastic leukemia in children. Curr opin oncol. 2000; 12:3-12; Miller R. Acute lymphocytic leukemia. In: C K Tebbi, editor. Major Topics in Pediatric and Adolescent Oncology. Boston: GK Hall Medical Publishers; 1982. p. 3-43). To date, despite numerous attempts, the cause of leukemia in childhood remains unknown, except for isolated cases. As outlined above, various etiologies such as viral infections, chemical exposure, medications, ionizing radiation chromosomal abnormalities/genetic factors, immune deficiency, environmental issues, etc. have been proposed, but none has been definitively proven or can be consistently applied to the majority of cases. The International Agency for Research on Cancer performed a retrospective study on leukemia occurrence in association with electrical power lines and found limited evidence that high levels of extremely low frequency magnetic fields may result in a twofold increased risk of some childhood leukemias, but this finding was later refuted (Non-Ionizing Radiation, Part 1: Static and Extremely Low-Frequency (ELF) Electric and Magnetic Fields (IARC Monographs on the Evaluation of the Carcinogenic Risks). Geneva: World Health Organization. pp. 332-333, 338, 2002; Kroll M E, et al., Childhood cancer and magnetic fields from high-voltage lines in England and Wales: a case-control study. Br J Cancer. 2010; 103 (7):1122-7; Little M P, et al., The statistical power of epidemiological studies analyzing the relationship between exposure to ionizing radiation and cancer, with special reference to childhood leukemia and natural background radiation. Radiat Res 2010; 174 (3):387-402).

Diagnosis of leukemia is usually based on complete blood counts, bone marrow examination by light microscopy, flow cytometric determination of cell surface phenotypes and other studies. In lymphomas, a lymph node biopsy can be performed for a diagnosis using pathology and flow cytometry, as well as other tests. Usually in leukemias and lymphomas, a cytogenetic evaluation is also performed and may have prognostic value. In acute leukemias and diffuse lymphomas, a spinal tap is required to rule out central nervous system involvement.

Most forms of acute lymphoblastic leukemias are treated with a multi-drug chemotherapy regimen, such as prednisone, L-asparaginase, vincristine, daunorubicin, antimetabolites, with or without radiation therapy (radiotherapy) to the central nervous system (Pui C H. Acute lymphoblastic leukemia in children. Curr opin oncol. 2000; 12:3-12). In some cases, during remission or after relapse, bone marrow transplantation may be required. The general goal of treatment is to obtain normal bone marrow production, called remission, and eliminate the systemic infiltration of organs by leukemic cells.

To date, the means of diagnosing leukemia has required highly skilled individuals and equipment analyzing various parameters, including bone marrow examinations, flow cytometry, and cytogenetics. These tests possess an inherent amount of uncertainty based on the technical expertise of the diagnosing physicians and technical staff and also require a significant amount of time to perform. No definitive laboratory test to predict predisposition to leukemia prior to its occurrence is currently available. Furthermore, there are no systemic screening tools to screen populations including infants and children. Additionally, there are no known methods for the prevention of leukemias and lymphomas in susceptible individuals. Accordingly, what is needed is a quick and reliable method to determine predisposition and diagnose leukemias and lymphomas, and screen for vaccines and compounds to prevent leukemia.

SUMMARY OF THE INVENTION

This invention uses cell surface markers and enzyme-linked-immunosorbent serologic assay (ELISA) to detect the potential for leukemia. It demonstrates that cell exposure to specific proteins can re-create cell surface markers in peripheral blood mononuclear cells of former leukemia patients which allows for the detection of leukemic potential. Likewise, the invention provides for the detection of leukemic potential by identifying antibodies present in the plasma of former leukemic patients and not "normal" individuals, which may relate to the cause of their disease. The results indicate that the methods presented herein may be used to identify patients who have leukemia, had leukemia, or are at risk to develop leukemia.

Cellular detection of leukemic potential is based on the novel finding that acute lymphoblastic leukemia (ALL) can be re-induced in former leukemic patients and those in remission or on therapy by exposure to supernatant of culture or purified protein of a fungal agent, i.e. *aspergillus flavus*, with or without a virus, e.g. Epstein-Barr virus (EBV), in vitro. Furthermore, a combination of *aspergillus flavus* and EBV induces a new protein which enhances development of cell surface markers characteristic of acute lymphoblastic leukemia (ALL) as detected by flow cytometry in mononuclear leukocyte cells of long-term survivors of ALL. This flow cytometry technique can detect propensity for development of leukemia markers in "susceptible" individuals. Supernatant of culture of *aspergillus flavus* or EBV, or their combination used in enzyme-linked-immunosorbent serologic assay (ELISA) technique can separate "normal" individuals from those of long-term survivors of ALL. These findings are unlike the indiscriminate effects of aflatoxins which do not separate normal individuals from former leukemic patients. These findings have implications for the etiology of leukemias and diffuse lymphomas. This invention can potentially be used for mass screening and detection of individuals susceptible to leukemia.

Fungi have been isolated from virtually all parts of the globe. *Aspergillus* species, such as *aspergillus flavus, parasiticus, nomius*, and others are widespread in nature and have been isolated from various environmental sources, including homes and food items such as greens, corn, peanuts, soybeans (Roze, et al., *Aspergillus* volatiles regulate Aflatoxin synthesis and asexual sporulation in *Aspergillus parasiticus*. Applied and Environmental Micro. 2007; 73 (22): 7268-7276). *Aspergillus* and other fungi are capable of producing various peptides and substances including ergot, alkaloids and aflatoxins (Kosalec I, and Pepeljnjak S. Mycotoxigenicity of clinical and environmental *Aspergillus fumigates* and *Aspergillus flavus* isolates. Acta Pharm. 2005; 55(4): 365-375; Roze, L V, et al., *Aspergillus* volatiles regulate Aflatoxin synthesis and asexual sporulation in *Aspergillus parasiticus*. Applied and Environmental Micro. 2007; 73(22): 7268-7276; Latge J P. *Aspergillus* fumigates and aspergillosis. Clin Microbiol Rev. 1999; 12:310-350; Fischer G, and Dott, W. Relevance of airborne fungi and their secondary metabolites for environmental, occupational and indoor hygiene. Arch Microbiol. 2003; 179:75-82; Fischer G, et al., Species-specific profiles of mycotoxins produced in cultures and associated with conidia of airborne fungi derived from biowaste. Int J Hyg Environ Health. 2000; 203:105-116; Raper K B, and Fennell D I. The genus *Aspergillus*. Baltimore: Williams & Wilkins; 1965; Stack D, et al., Nonribosomal peptide synthesis in *Aspergillus* fumigates and other fungi. Microbiology. 2007; 153:1297-1306; Yang C V, et al., Inhibition of ebselen on aflatoxin B1-induced hepatocarcinogenesis in Fischer 355 rats. Carcinogenesis. 2000; 21 (12):2237-2243; Ito, Y, et al., *Aspergillus pseudotamarii*, a new aflatoxin producing species in *Aspergillus* section Flavi. Mycol Res. 2001; 105 (2):233-239; Matsumura M, Mori T: Detection of aflatoxins in autopsied materials from a patient infected with *Aspergillus flavus*. Nippon Ishinkin Gakkai Zasshi. 1998; 39 (3): 167-71; Louria D B, et al., Aflatoxin-induced tumors in mice. Medical Mycology. 1974; 12(3): 371-375; Cole R J, et al., Mycotoxins produced by *Aspergillus* fumigates species isolated from molded silage. J Agric Food Chem. 1977; 25:826-830). Aflatoxins are potent, naturally occurring mycotoxins produced by many species of *aspergillus*, including *aspergillus flavus*. At least thirteen subtypes of aflatoxins have been identified, with B1 being the most toxic. Both aflatoxin B1 and B2 are produced by *aspergillus flavus*. Humans are frequently exposed to *aspergillus* species which are generally widespread in the environment. Aflatoxins are known to be metabolized by the liver. Carcinogenesis and infections induced by various strains of *aspergillus* are well recognized (Louria D B, et al., Aflatoxin-induced tumors in mice. Medical Mycology. 1974; 12(3): 371-375; Yarborough, A, e al., Immunoperoxidase detection of 8-hydroxydeoxyguanosine in Aflatoxin B1-treated rat liver and human oral mucosal cells. Cancer Research. 1996; 56:683-688)

Epstein-Barr virus (human herpesvirus 4, HHV-4 or EBV), a member of the herpesvirus family, is one of the most common viral agents affecting humans. Various strains of this virus occur worldwide. EBV infects B-lymphocytes. In vitro, infection results in transformation of lymphocytes which, in turn, express novel proteins. EBNA-2, EBNA-3C and LMP-1 are essential for transformation, while others, such as EBNA-LP and EBERs are not involved in this process. EBNA-1 protein is needed to maintain the viral genome. While acute infections, the hallmark of this virus, are well known, chronic "inactive" persistence with periodical resurgence and reactivation can occur. EBV nuclear proteins are produced by alternative splicing of a transcript starting at either the Cp or Wp promoters at the left end of the genome. The genes are EBNA-LP/EBNA-2/EBNA-3A/EBNA-3B/EBNA-3C/EBNA-1 within the genome.

EBV has been associated with carcinogenesis (Tokunaga M, Imai S, Uemura T Tokudome, Osato T, and Sato E. Epstein-Barr virus in adult T-cell leukemia/lymphoma. Am J Pathol. 1993; 143(5): 1263-1268), autoimmune disorders, infections and even diabetes mellitus. Most individuals are infected by this virus by the time they reach adulthood. In the United States, the rate of prior exposure to this agent in adults over age 35 is 95%. When the disease occurs in adolescents and adults, it only causes symptoms of infectious mononucleosis in 50% of infected individuals (CDC Data 2010).

The effects of simultaneous exposure to *aspergillus flavus* and Epstein-Barr Virus in humans, as well as gene-environment interaction to each agent and their combination, heretofore has not been described.

The studies described herein reveal that mononuclear cells obtained from the peripheral blood of patients with ALL react when exposed to supernatant of *aspergillus flavus* culture or EBV sources or a combination of the two, by forming blast cells which, by cell surface phenotyping, are indistinguishable from leukemia cells. This phenomenon is seen in patients currently on therapy and those off treatment, including some who have been treated many years prior to this investigation. The exposed cells demonstrate cell surface phenotypes (CD10/19, CD34/CD19, CD34/CD117) which are hallmarks of acute lymphoblastic leukemia. Such reaction is enhanced by the addition of supernatant of ICL87 culture which contains Epstein-Barr virus (EBV) or the addition of purified EBV virus, with and without incubation. Controls, including mononuclear white blood cells from normal individuals and patients with sickle cell (SC) disease did not show a similar reaction. By ELISA technique, the plasma of the ALL patients was found to react with the supernatant of cultures of *aspergillus flavus*. Similar results were not obtained when cells from "normal" persons (controls), e.g. normal donors and patients with sickle cell disease, or individuals with solid tumors, treated in vitro on an identical basis. A statistically clear separation of leukemic and "normal" controls was obtained. Radiation of cultures containing *aspergillus flavus*, with or without EBV, resulted in enhancement of the described effects. Substitution of the supernatant of culture of *aspergillus flavus* with *mycocladus corymbifera* species (SB) or purified commercially available aflatoxin B1 (AT) and replacement of EBV with avian leukosis virus (cV) did not result in similar discriminative changes in cells from leukemia patients in remission and normal individuals' cells. Substitution with plasma (pl), or supernatant of owl monkey 1C3 B-lymphoblast cell line (CRL-2312) (OM) did not induce development of ALL surface markers. Further experiments reveal that the development of leukemic cell surface phenotypes occurs gradually, starting two hours after incubation with *aspergillus flavus*, with or without Epstein-Barr Virus, and is complete after 24 hours of incubation. No changes are seen in normal controls.

When analyzed with Fast Protein Liquid Chromatography (FPLC), supernatant of *aspergillus flavus* (X) contains three peaks of protein. EBV produces one protein peak. Addition of EBV with short (less than four hours) or long (seven days) incubation enhances the first peak of *aspergillus flavus* protein and induces development of an additional new peak. Furthermore, radiation of *aspergillus flavus* alone or when combined with EBV induces further increases in the inductive abilities of the *aspergillus flavus* first-peak fraction in former leukemic patients, and not in controls. After radiation, the effects of fractions from peaks 2 and 3 remain unchanged. A comparison of *aspergillus flavus* peaks, EBV peak, and the combination thereof is shown in FIGS. 1 through 3. While fractions from the first peak have the most potency, the other two are also effective in inducing leukemic cell markers in susceptible cells, and detection by ELISA technique. These substances can induce leukemic markers in formerly leukemic patients, but not in controls. Testing of these peaks indicates that they are also useful for serologic detection of patients predisposed to leukemia with the first peak having the most activity.

The aforementioned experiments describe induction of cell surface phenotypes, characteristic of acute lymphoblastic leukemia or diffuse lymphomas, upon exposure to supernatant of culture of *aspergillus flavus* or EBV or combination thereof in patients who have been in long-term remission or "cured" of these disorders. The latter effect is enhanced when cells are exposed to the combination of both agents, or when the combination of agents is irradiated prior to incubation with the mononuclear cells from patients in remission or "cured" of leukemia or lymphoma. These effects could not be duplicated in normal controls or patients with solid tumors. The discriminative effect seen with these agents were not observed with purified aflatoxin B, avian leukosis virus or other agents used as controls. The study also describes detection of antibodies to *aspergillus flavus* and EBV and a combination thereof in plasma of patients with acute lymphoblastic leukemia and diffuse lymphomas and not in patients with solid tumors or controls. These findings indicate that individuals with acute lymphoblastic leukemia or diffuse lymphomas may have a distinct genotype, allowing leukemic markers to be re-induced upon certain exposures. Gene-environmental interactions with *aspergillus flavus* with or without a viral agent are proposed to cause phenotypes specific to these diseases or recurrences thereof. The findings have implications for the etiology of cancer in general and acute lymphoblastic leukemia/diffuse lymphoma in particular.

The effect seen herein appears to be unique to *Aspergillus flavus* or to EBV, which discriminately induce the expression of leukemic markers of the cell surface of individuals with leukemia, individuals who have been cured for leukemia, and individuals having the potential to become leukemic. Other compositions do not discriminate between individuals having leukemia or those who have had leukemia, and those who are not at risk. For example, aflotoxin induces expression of leukemic markers on cell surfaces but does so to all samples, while other viruses like owl monkey virus do not induce marker expression. As such, the tests used herein rely on the novel ability of *Aspergillus flavus* and/or EBV to provide the cell surface marker induction.

BRIEF DESCRIPTION OF THE DRAWINGS

For fuller understanding of the invention, reference should be made to the following detailed description, taken in connection with the accompanying drawings, in which.

Figure 12:
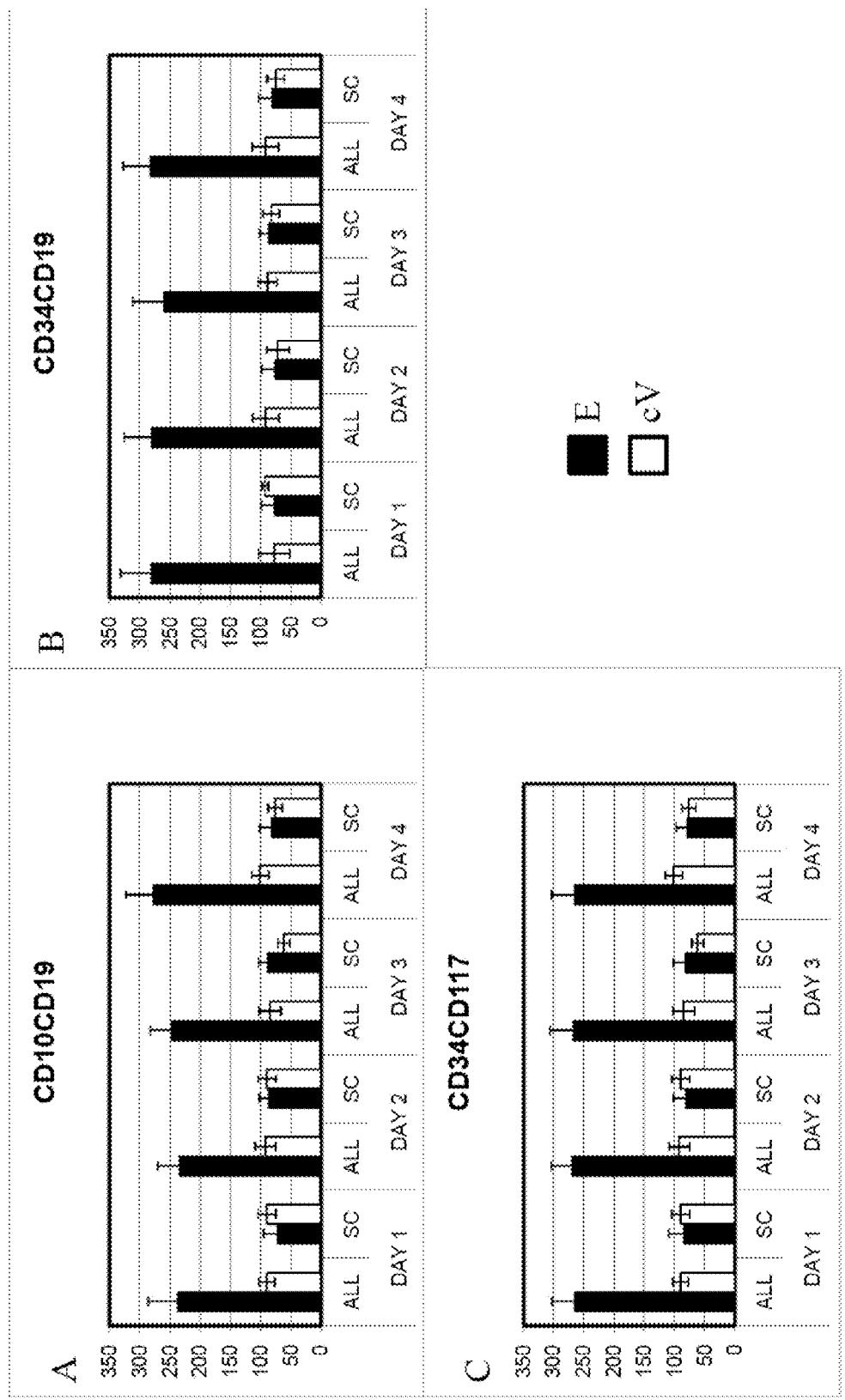

FIGS. 12(A)-(C) are graphs showing cellular surface phenotyping from individuals who are long-term survivors of leukemia (ALL) exposed to Epstein-Barr Virus obtained from culture of CCL-87 cells (E) as compared to avian leukosis virus (cV). The cultures are evaluated daily from day 1-4 post-incubation. Controls are mononuclear cells from "normal"/sickle cell (SC) patients.

Figure 13:
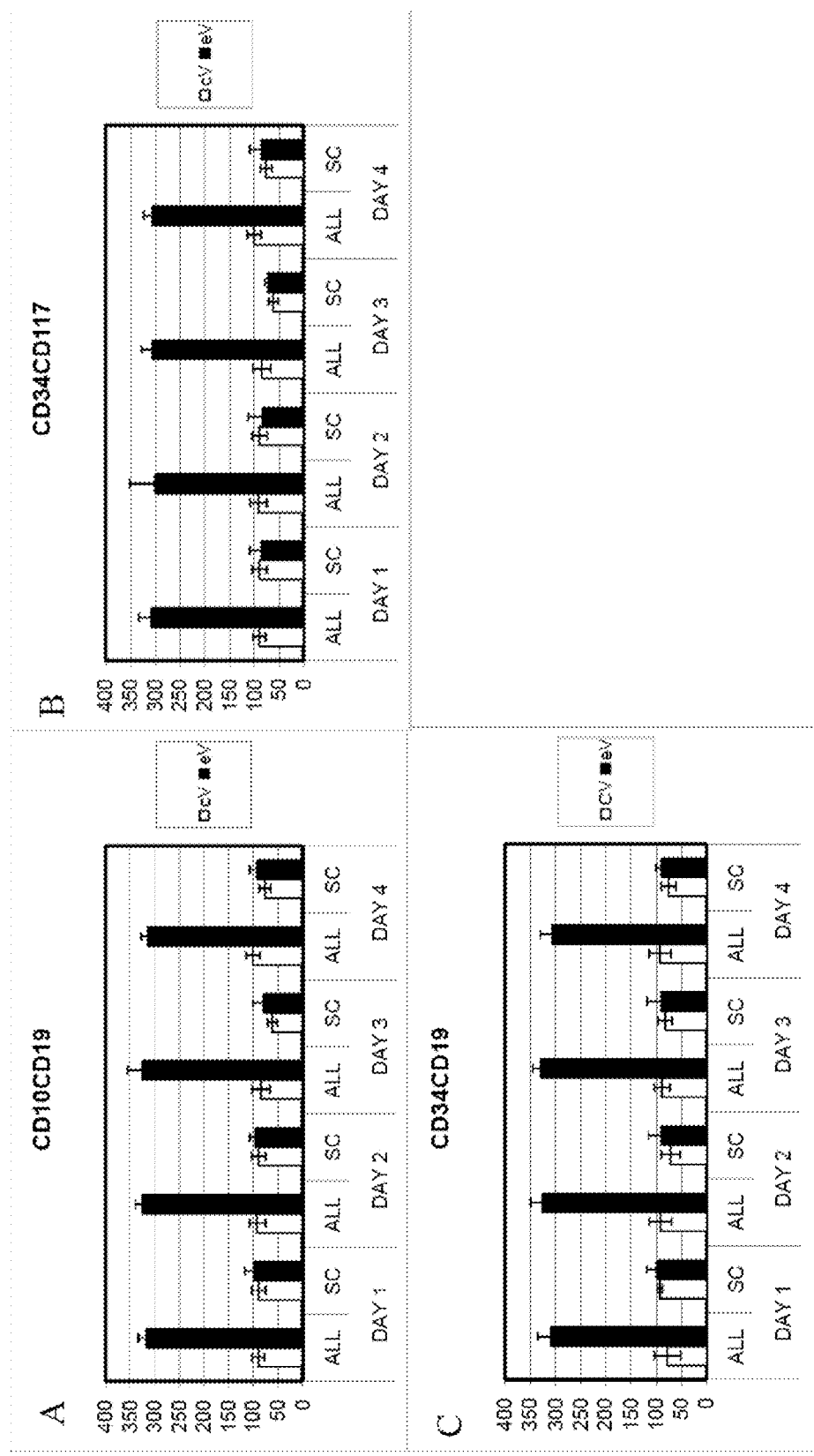

FIGS. 13(A)-(C) are graphs showing cellular surface phenotypes of cells from leukemic patients (ALL) and "normal"/sickle cell samples (SC) (controls). Cells were incubated with either purified Epstein-Barr Virus at $2 \times 10^6$ PFU/ml (eV) or avian leukosis virus at $2 \times 10^6$ PFU/ml (cV) and detected at days 1-4 post-incubation.

Figure 14:
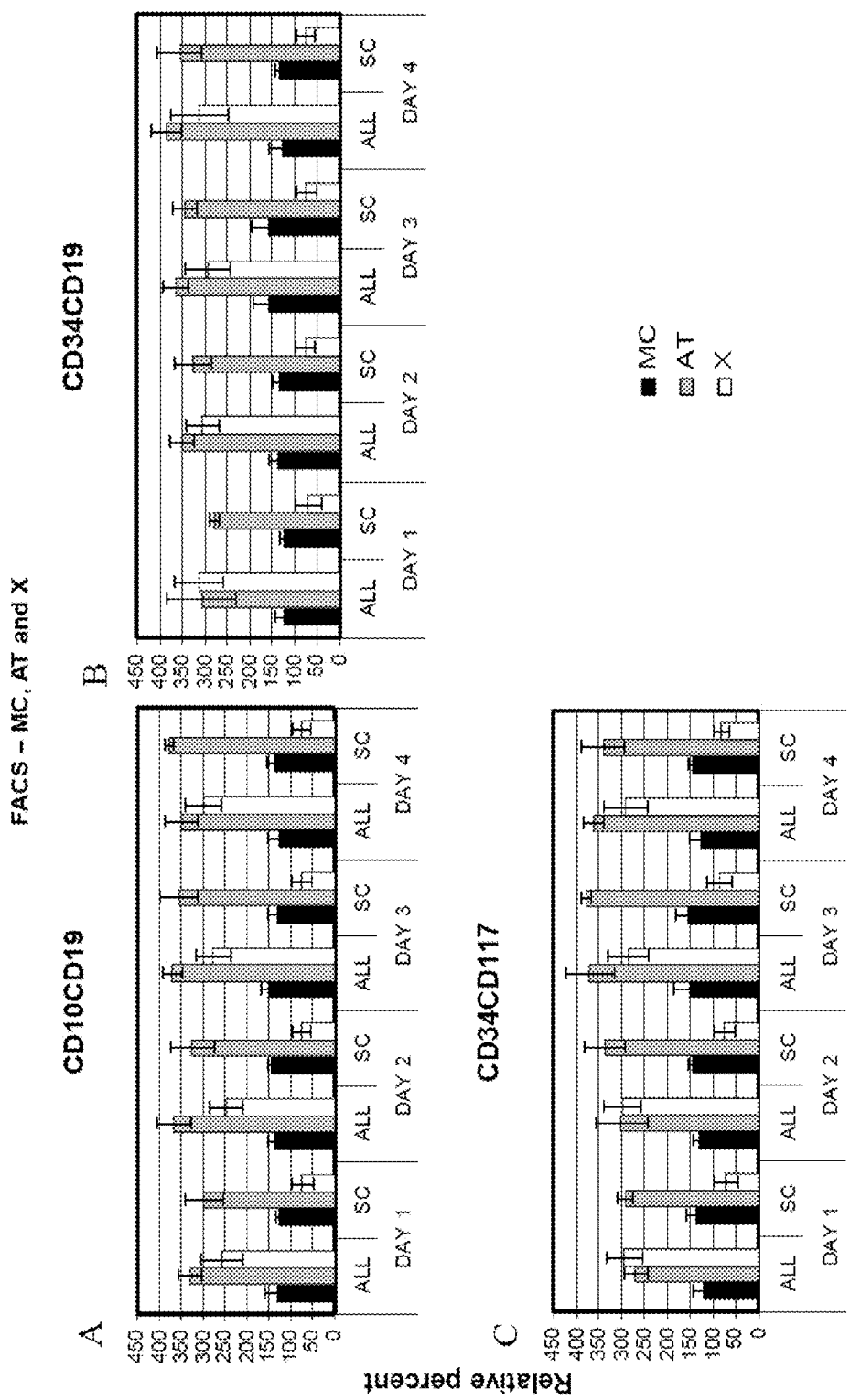

FIGS. 14(A)-(C) are graphs comparing effects of the supernatant of culture of *aspergillus flavus* (X) and *mycocladus corymbifera* (MC), another fungal agent, and aflatoxin (AT), on development of cell surface phenotype, characteristic of acute lymphoblastic leukemia (ALL) in mononuclear leukocytes of patients in long-term remission of ALL and "normal"/sickle cell patients ("normal controls"). Results are shown in columns with standard deviation.

Figure 15B:
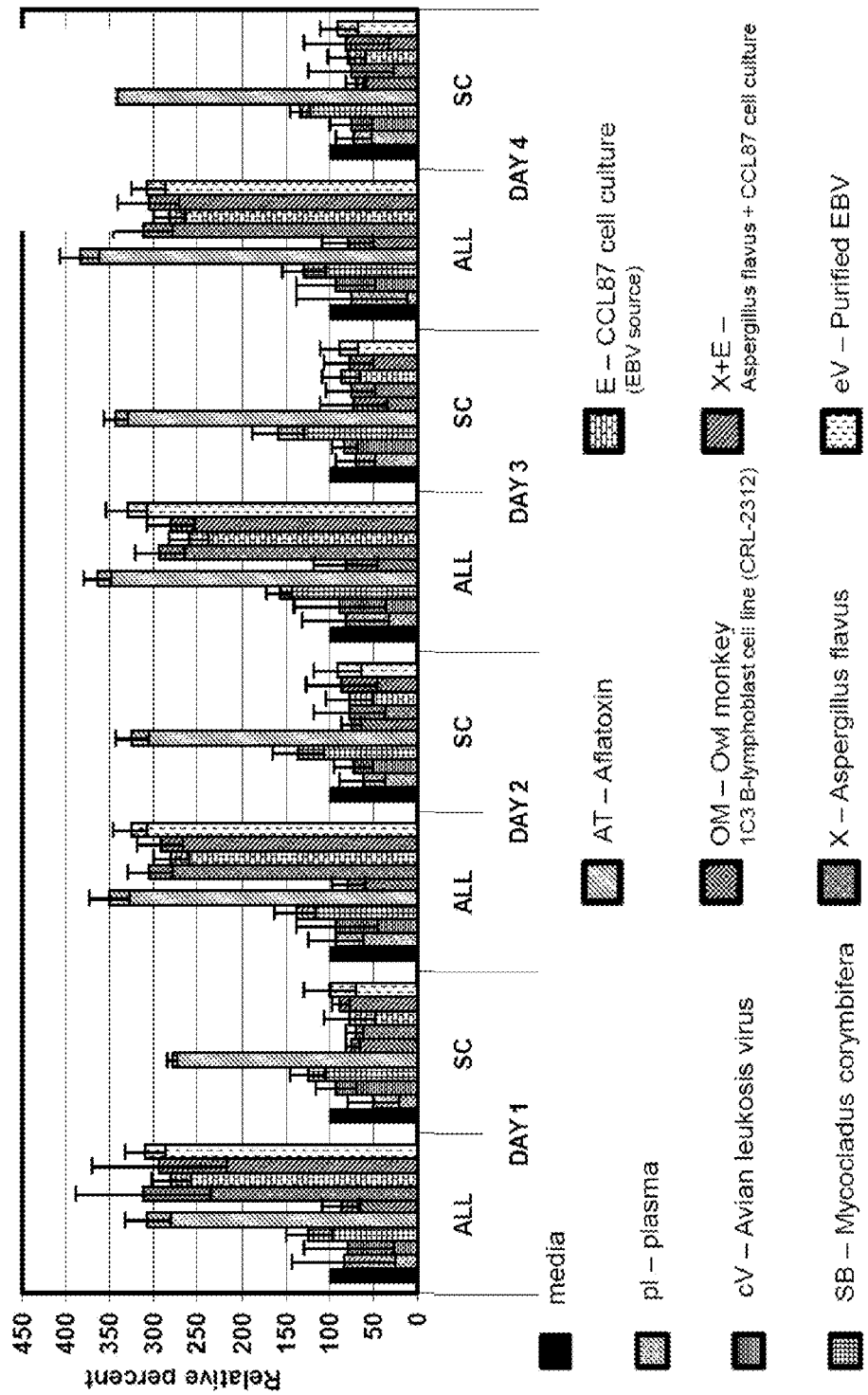
Figure 15C:
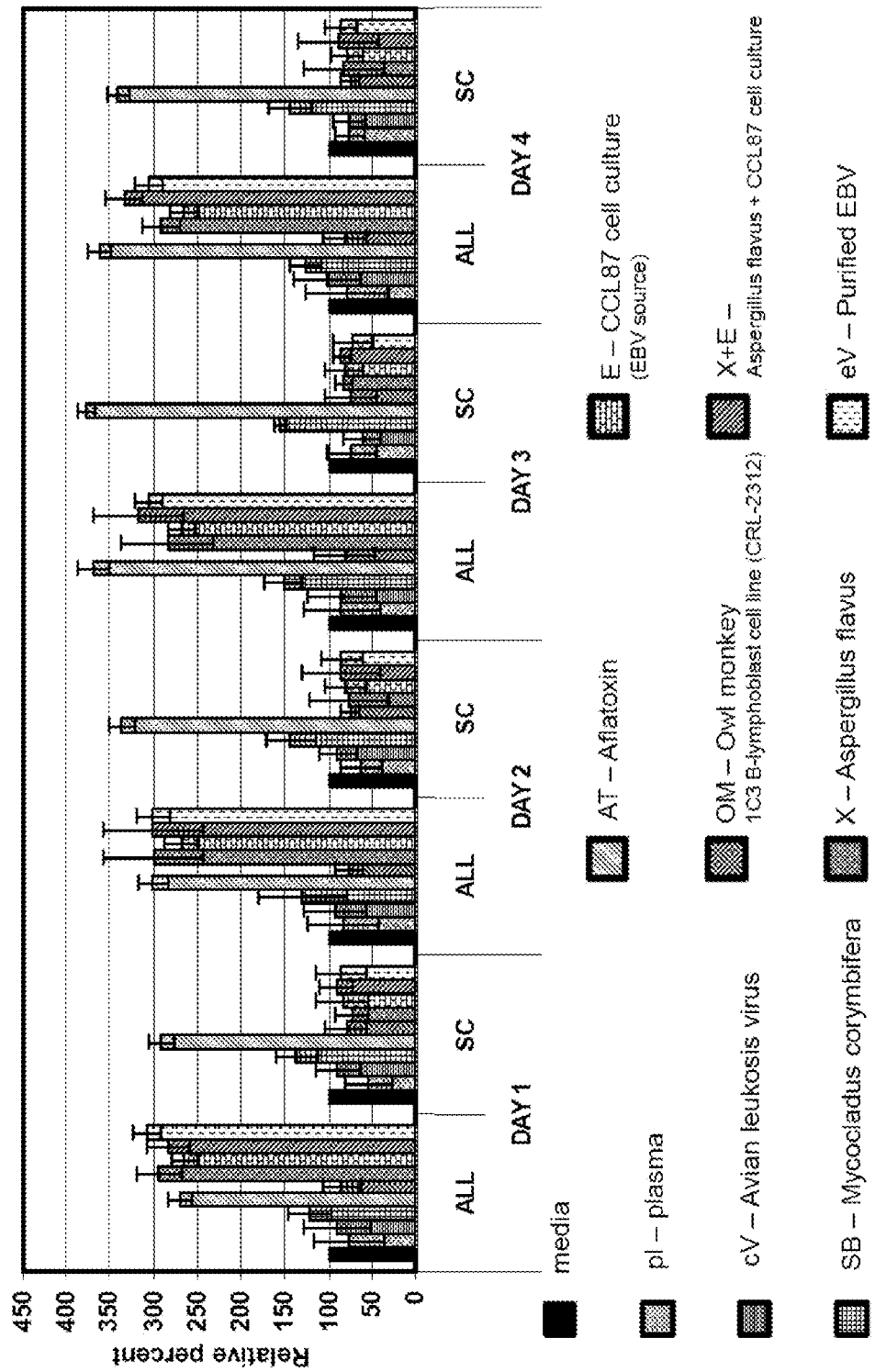

FIGS. 15(A)-(C) are graphs showing a summary of cell surface phenotyping for (A) CD10/CD19, (B) CD34/CD19, and (C) CD34/CD117 of mononuclear leukocytes of individuals who are long term survivors of leukemia (ALL) incubated with media, plasma (pl), Avian leukosis virus (cV), *mycocladus corymbifera* (SB), aflatoxin (AT), Owl monkey cells (CRL-2312 culture) (OM), *aspergillus flavus* (X), CCL87 (E), *aspergillus flavus*+CCL87 (X+E), and purified EBV (eV). The cultures were evaluated daily from day 1-4 post-incubation. Controls are mononuclear cells from "normal"/sickle cell patients.

Figure 16:
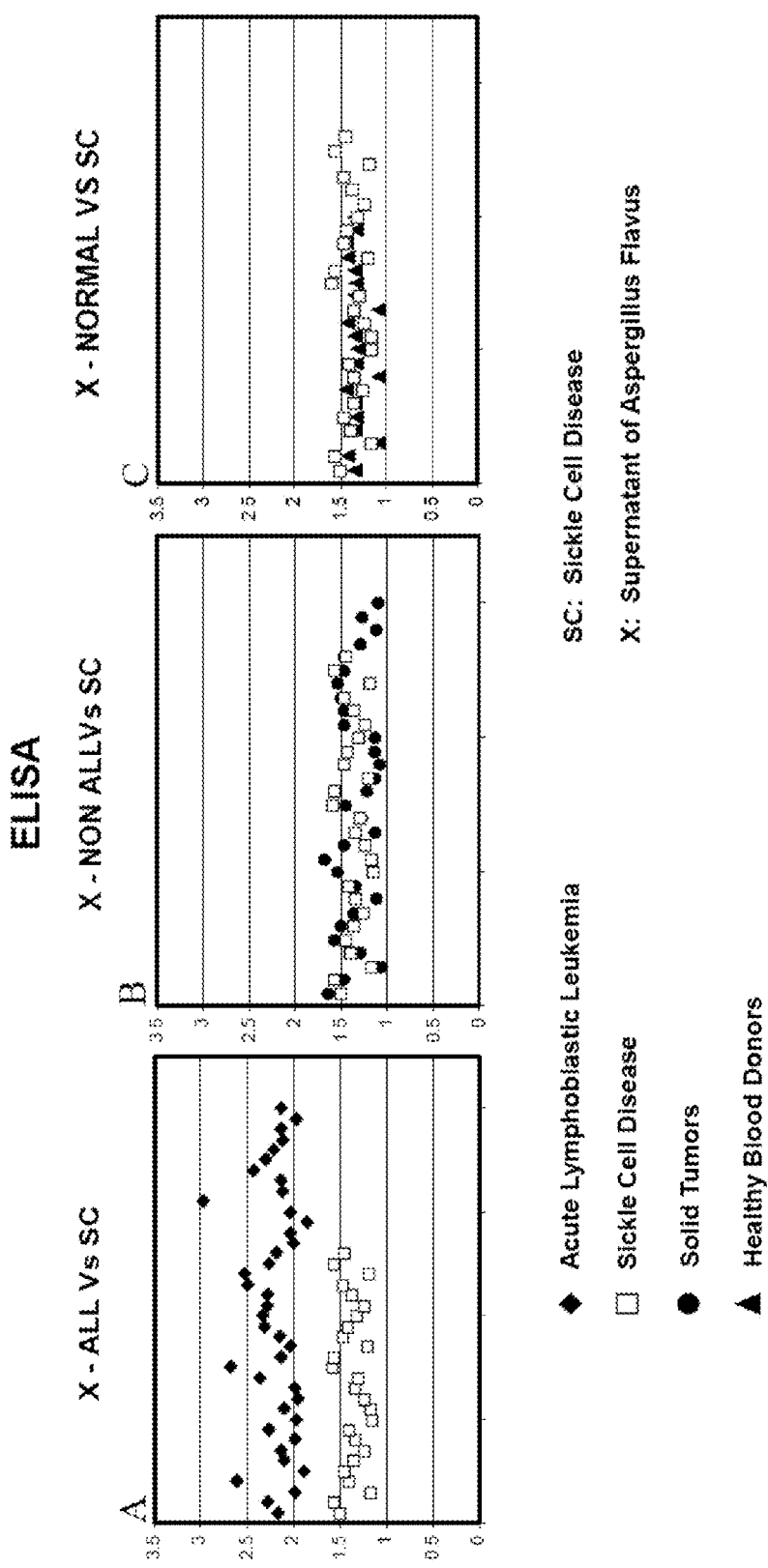

FIGS. 16(A)-(C) are graphs showing ELISA detection indicating a difference in long-term survivor leukemia patients compared to non-leukemic samples. (A) The supernatant from *aspergillus flavus* fungal culture (X) was incubated with ALL leukemic patients' plasma as compared to SC ("normal" controls); (B) The supernatant from *aspergillus flavus* fungal culture (X) was incubated with non-ALL cancer patients (solid tumors) as compared to SC ("normal" controls); (C) The supernatant from *aspergillus flavus* fungal culture (X) was incubated with normal human samples from normal blood donors (discarded blood from blood bank), and compared to sickle cell patients' (SC) plasma.

Figure 17:
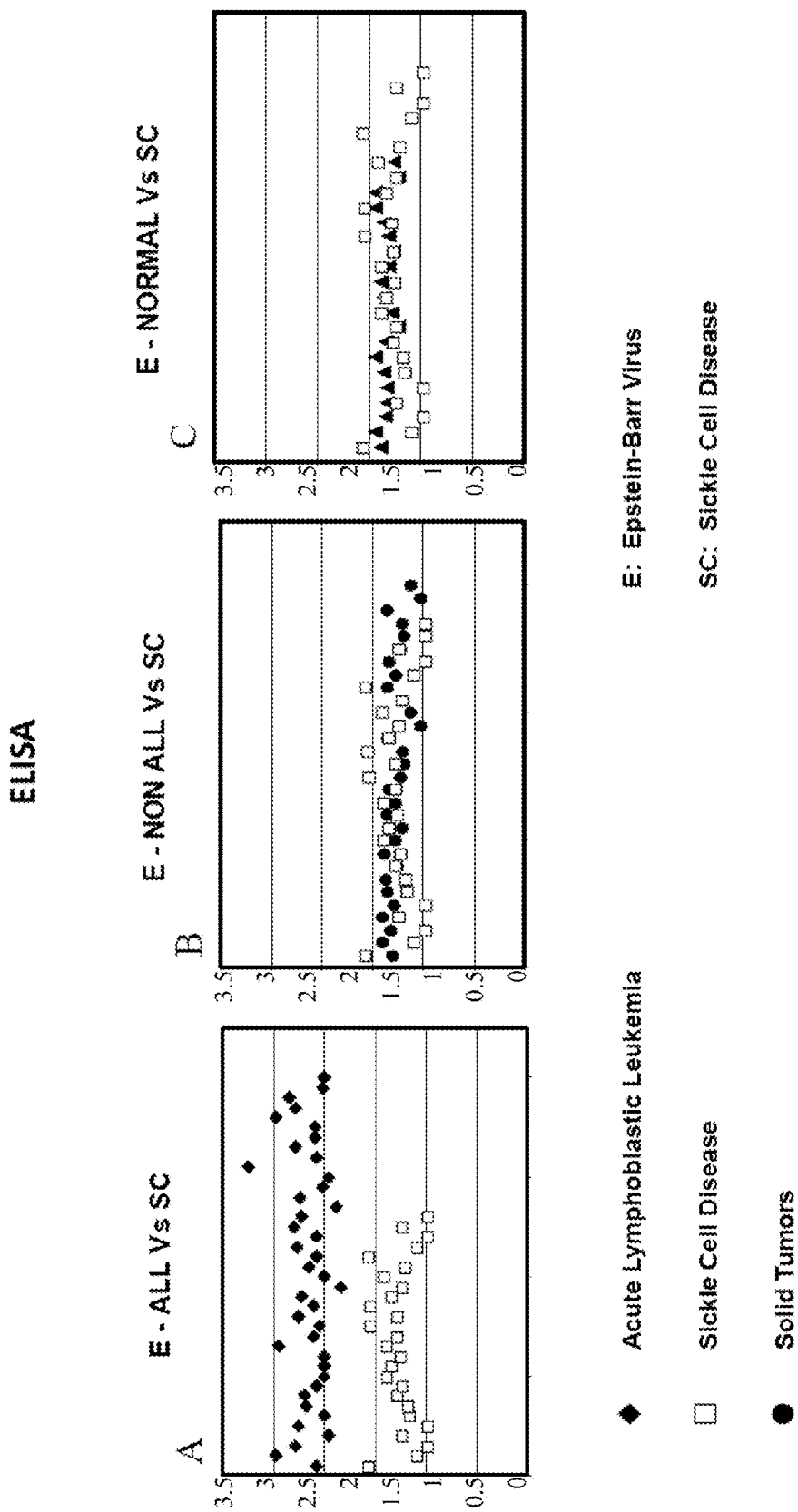
Figure 18:
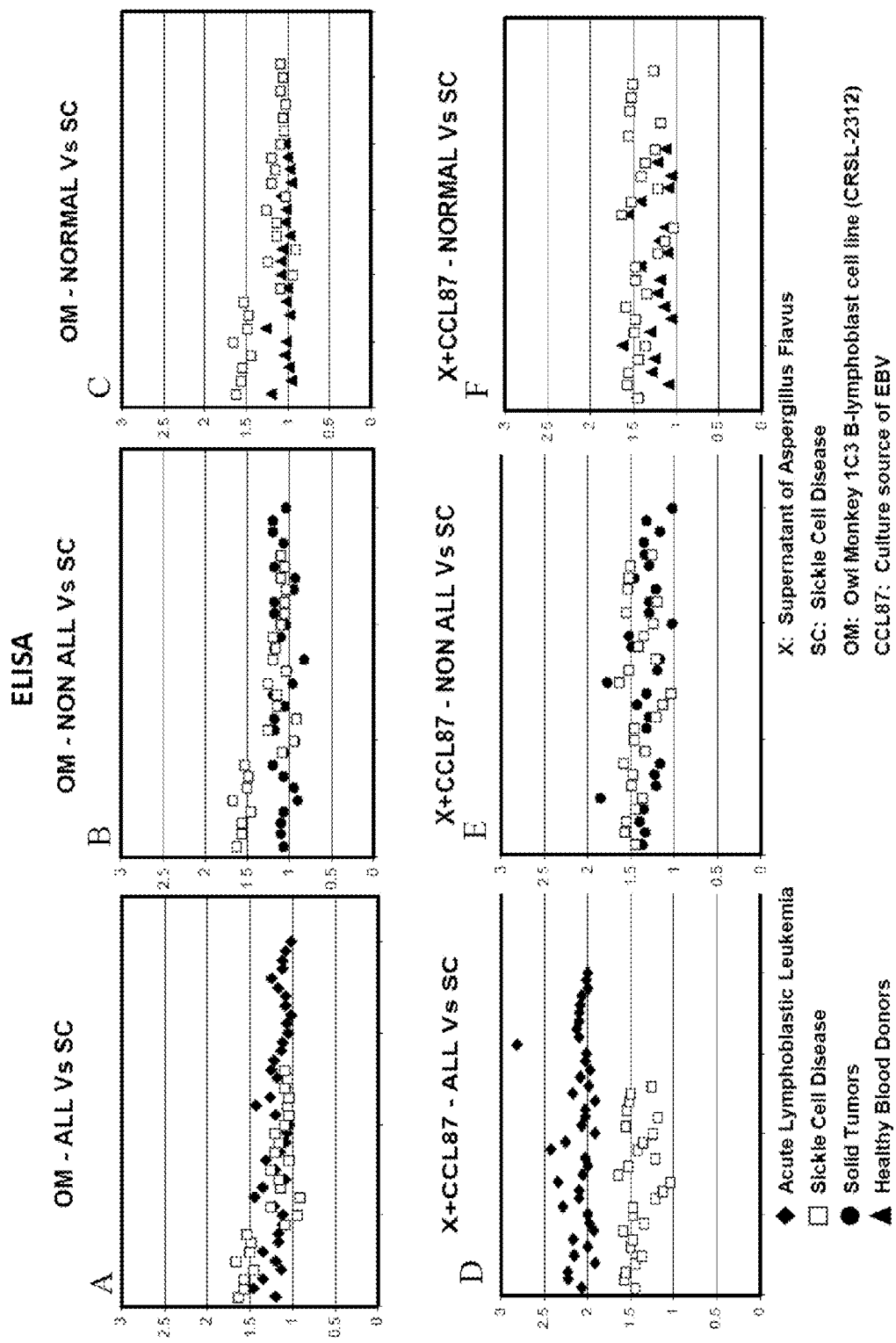

FIGS. 17(A)-(C) are graphs showing ELISA detection, indicating a difference in leukemic patients compared to non-leukemic samples. (A) The supernatant from EBV-infected CCL-87 culture (E) was incubated with plasma of patients who are long term survivors of acute lymphoblastic leukemia (ALL) in remission and compared to SC ("normal" controls); (B) the supernatant from EBV-infected CCL-87 culture (E) was incubated with non-ALL cancer patients (solid tumors) and compared to SC ("normal" controls); (C) the supernatant from EBV-infected CCL-87 culture (E) was incubated with normal blood donor plasma (discarded plasma from blood bank) and compared to SC ("normal" controls).

FIGS. 18(A)-(F) are graphs showing that ELISA technique, using supernatant of owl monkey 1C3 B-lymphoblast cell line (CRL-2312) cell culture (OM), can not differentiate plasma from acute lymphoblastic leukemia (ALL) from that of "normal"/sickle cell (SC) patients (A), solid tumor patients (B) or normal plasma discarded from a blood bank, i.e. "normal" donors (C).

Combination of supernatant *aspergillus flavus* culture (X) added to culture of CCL-87 containing EBV (CCL87) can detect acute lymphoblastic leukemia patients in long term remission from normal controls/sickle cell patients (D). Plasma of solid tumor patients (non-ALL) and normal controls can not be differentiated by this X+CCL87 combination (E). Using X+CCL-87, plasma of sickle cell (SC) patients is indistinguishable from that of random healthy blood donors (F).

Figure 19A:
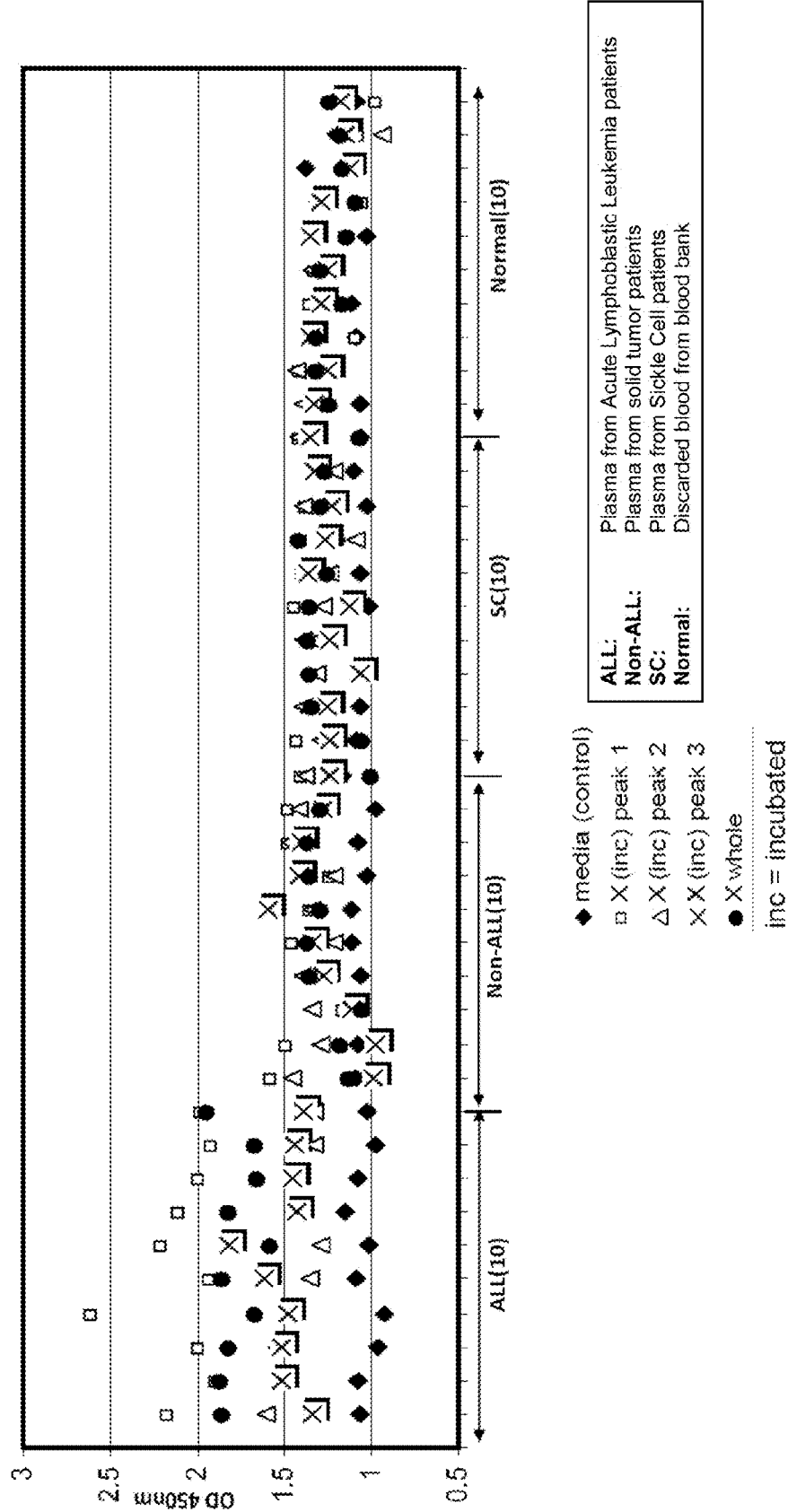
Figure 19B:
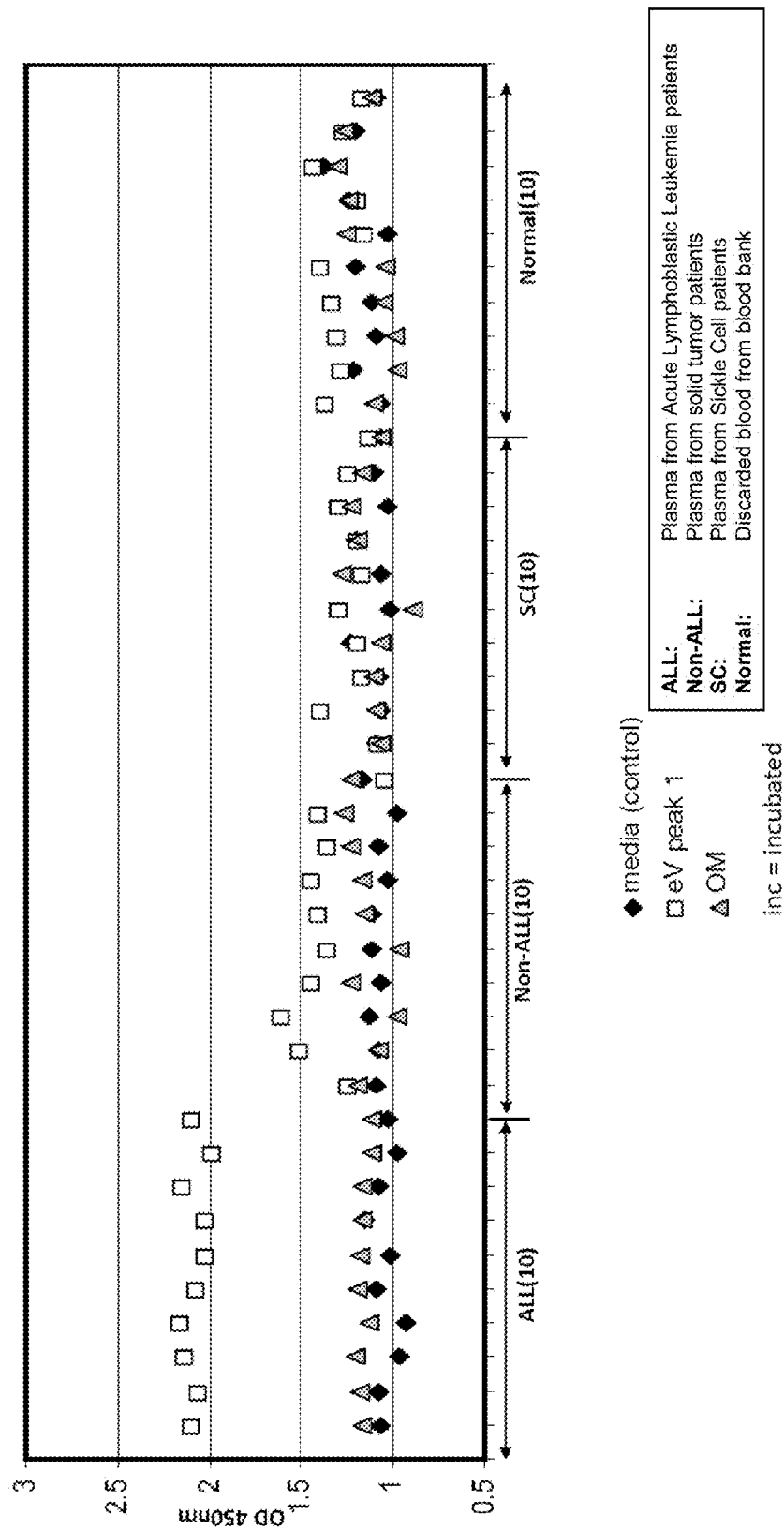
Figure 19C:
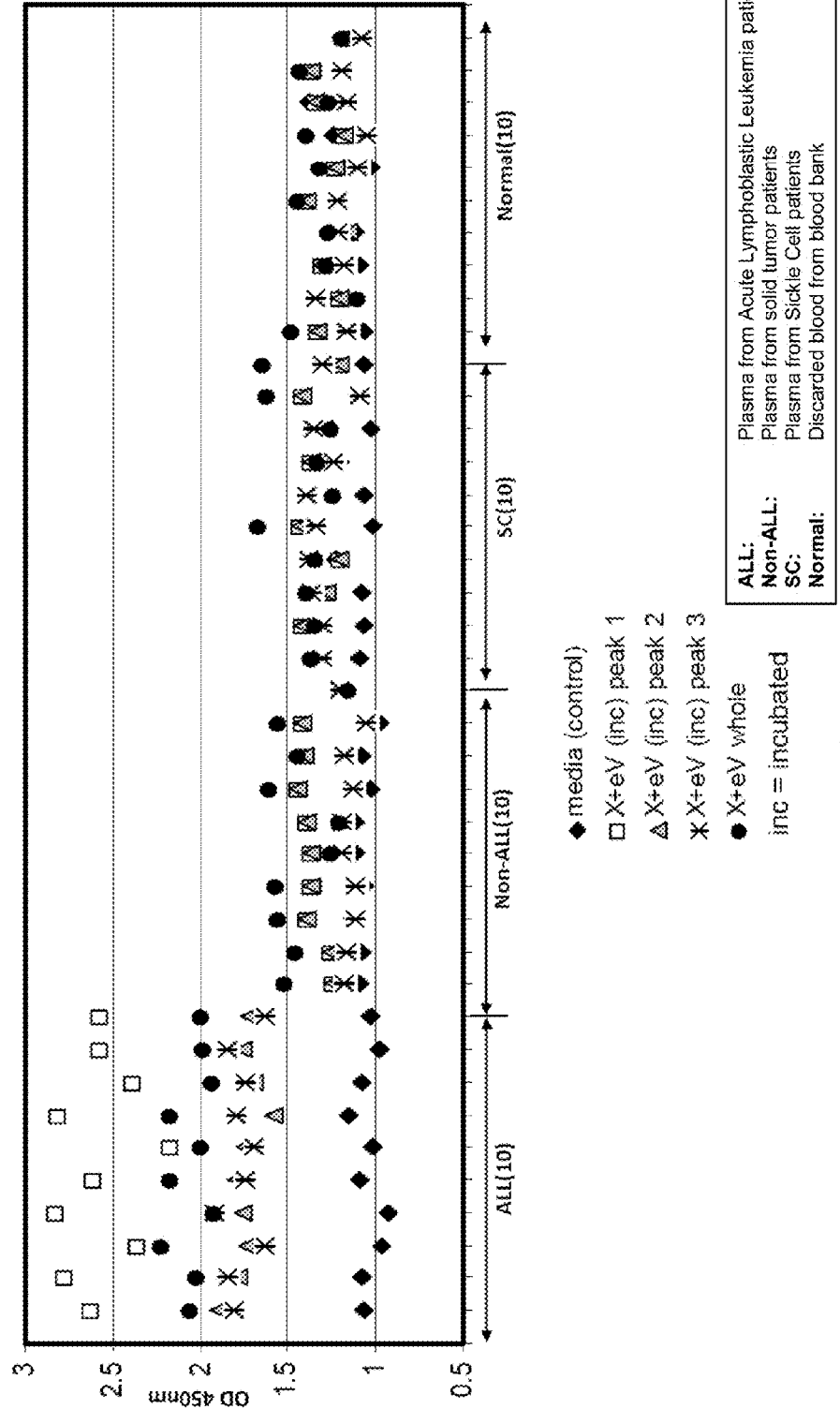

FIGS. 19(A)-(C) are graphs showing ELISA detection using peaks from protein analysis of the supernatant of *aspergillus flavus* alone, Epstein-Barr virus, and a combination thereof with incubation.

Figure 20A:
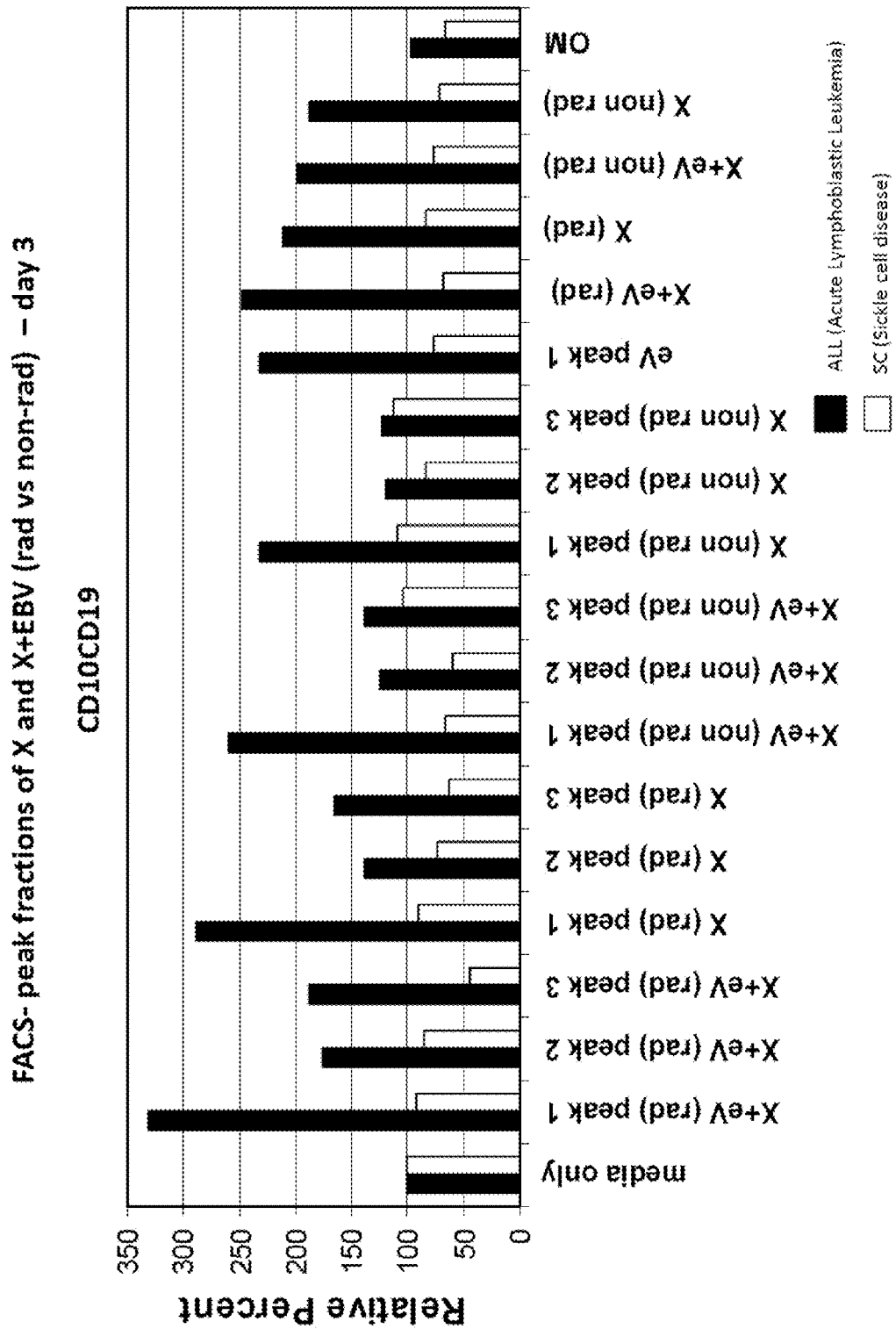
Figure 20B:
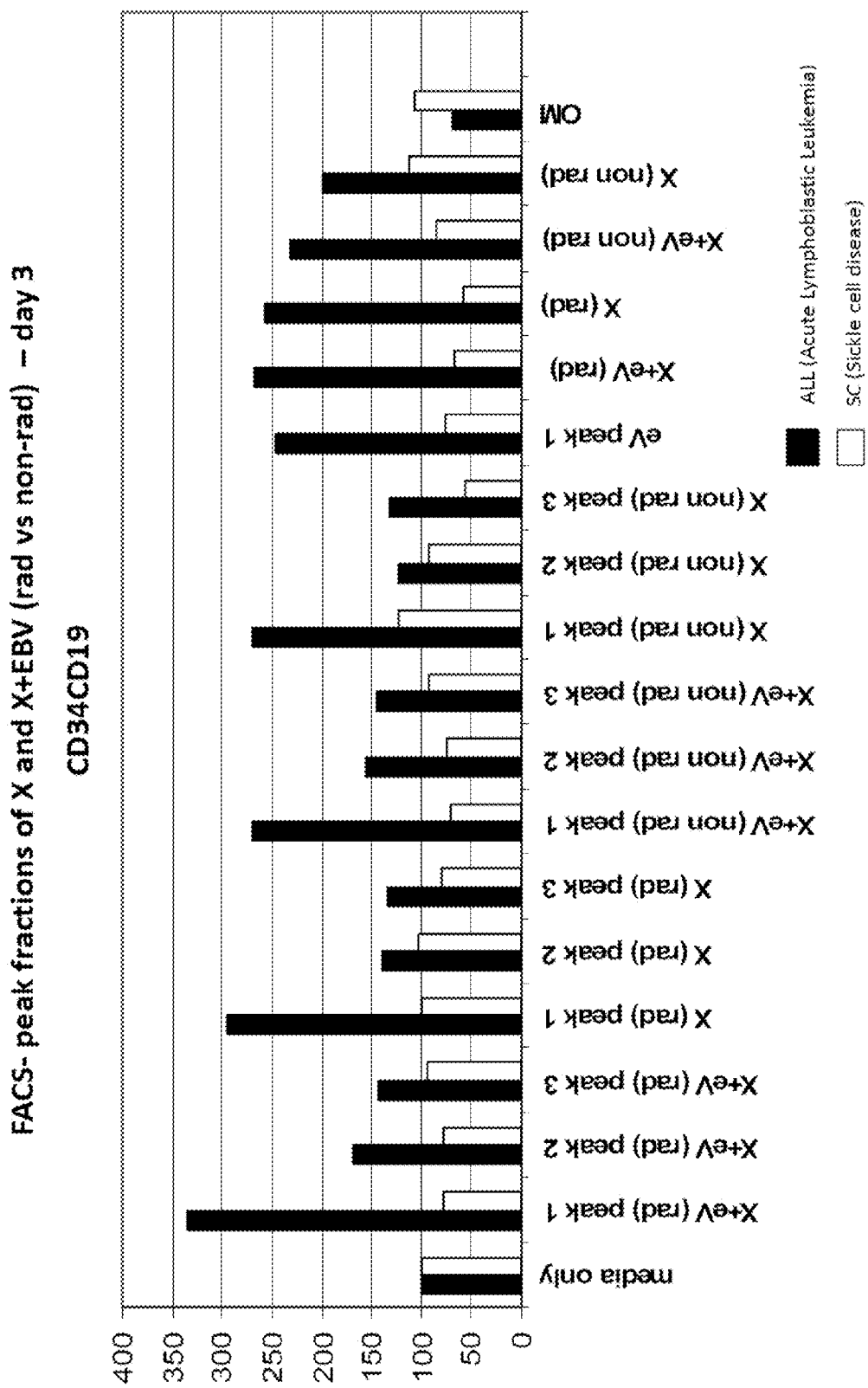
Figure 20C:
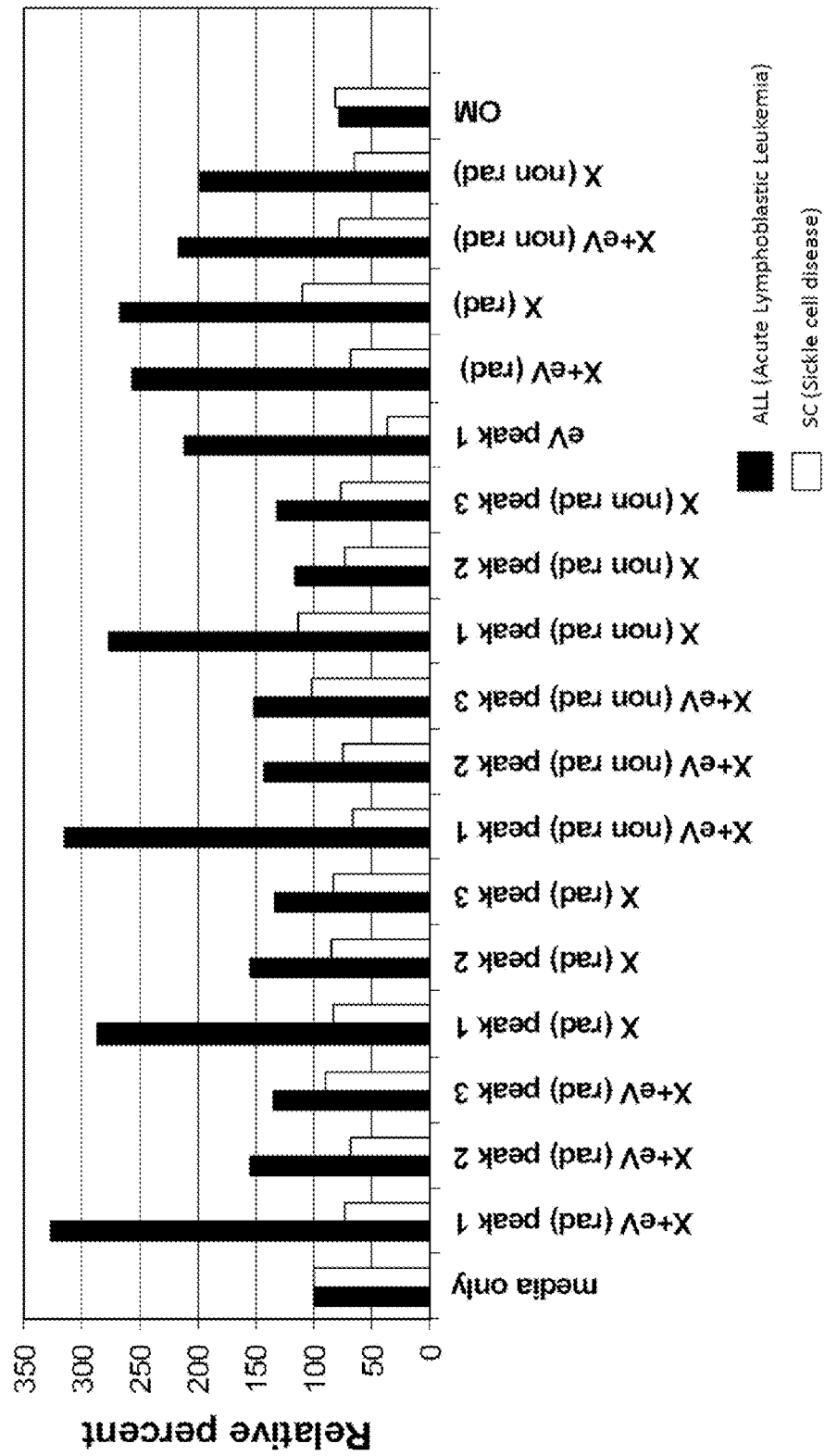

FIGS. 20(A)-(C) are graphs showing the effects of isolated peaks 1, 2, 3 of the supernatant of *aspergillus flavus* alone or in combination with Epstein-Barr Virus (EBV) with and without 50 cGy irradiation on the development of cell surface markers characteristic of acute lymphoblastic leukemia in former leukemia patients and controls (SC). All data are shown as percentage of controls.

FIGS. 21(A)-(C) are graphs showing cell surface phenotyping of blood mononuclear cells. Cells were obtained from individuals who are long-term survivors of leukemia exposed to supernatant of *aspergillus flavus* culture (X) as compared to EBV-infected CCL-87 culture (CCL87), purified EBV, or avian leukosis virus (cV). The cultures were evaluated daily from day 1-4 post-incubation. Controls are mononuclear cells from "normal"/sickle-cell patients.

FIGS. 22(A)-(B) reveal gradual development of leukemic cell surface phenotype CD10/CD19 after one, two, three, four, five, six, and 24 hours of incubation with *aspergillus flavus* (X), Epstein-Barr Virus (eV), combination of X and eV (X+eV), as compared to control (media only). Cell surface markers CD10/CD19, or (B) CD19/CD34 were evaluated for patients in long-term remission of leukemia (ALL) (A) versus "normal"/sickle cell controls (SC) (B). All data are shown as percentage of controls with standard deviation.

FIGS. 23(A)-(B) reveal gradual development of leukemic cell surface phenotype CD19/CD34 after one, two, three, four, five, six, and 24 hours of incubation with *aspergillus flavus* (X), Epstein-Barr Virus (eV), combination of X and eV (X+eV), as compared to control (media only). Cell surface markers CD19/CD34 were evaluated for patients in long-term remission of leukemia (ALL) (A) versus "normal"/sickle cell controls (SC) (B). All data are shown as percentage of controls.

Figure 24:
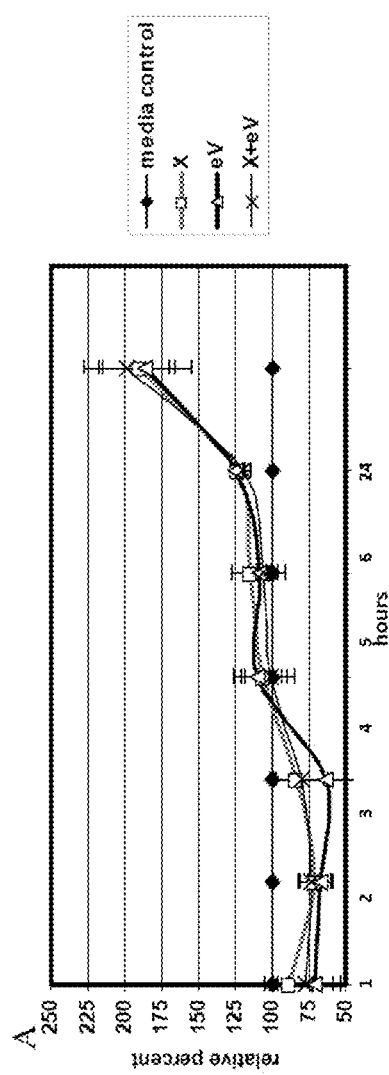
Figure 24:
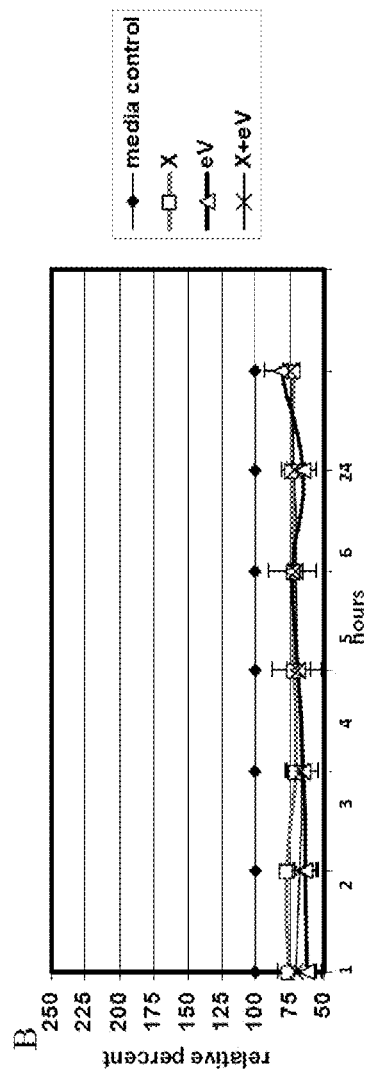

FIGS. 24(A)-(B) reveal gradual development of leukemic cell surface phenotype CD34/CD117 after one, two, three, four, five, six, and 24 hours of incubation with *aspergillus flavus* (X), Epstein-Barr Virus (eV), combination of X and eV (X+eV), as compared to control (media only). Cell surface markers CD34/CD117 were evaluated in patients in long-term remission of leukemia (ALL) (A) versus "normal"/sickle cell controls (SC) (B). All data are shown as percentage of controls with standard deviation.

DETAILED DESCRIPTION OF THE PREFERRED EMBODIMENT

These studies indicate that exposure to supernatant of *aspergillus flavus* and EBV, solely or in combination, can in vitro re-induce leukemic phenotype in mononuclear leukocytes of long-term remission patients with ALL and not in controls, including patients with solid tumors. These studies shed light on the effects of these agents in generation of acute lymphoblastic leukemia in genetically susceptible patients.

As used herein, "diagnosing" acute lymphoblastic leukemia refers to classifying a medical condition, predicting or prognosticating whether a particular abnormal condition will likely occur or will recur after treatment based on an indicia, detecting the occurrence of the disease in an individual, determining severity of such a disease, and monitoring disease progression.

As used herein, "individual" denotes a member of the mammalian species and includes humans, primates, mice and domestic animals such as cattle and sheep.

As used herein, "leukemic patient" means any individual diagnosed or previously diagnosed as having acute lymphoblastic leukemia/diffuse lymphoma. This includes individuals previously treated for acute lymphoblastic leukemia/diffuse lymphoma, and displaying long term remission of leukemia.

As used herein, non-leukemic patients means any individuals diagnosed or previously diagnosed as having solid tumors other than leukemia/diffuse lymphoma.

As used herein, "detection" means determining or identifying the presence of the detectable antibody by ELISA technique or induction of cell surface phenotypes characteristic of acute lymphoblastic leukemia on mononuclear leukocytes.

As used herein, "antibody" or "antibodies" are used in a broad sense and include proteins as described, monoclonal antibodies, polyclonal antibodies, multispecific antibodies, and antibody fragments.

Standard methodologies for all cultures, techniques, ELISA, flow cytometry, FPLC, gel electrophoresis and protein determination were used.

Example 1

Four isolates of *aspergillus flavus* were collected from separate homes of patients diagnosed with ALL over a period of 45 years. All four isolates proved to have identical properties and similar effects on cell transformation. Therefore, filtered supernatant of only one isolate (UGB), characterized by its high growth rates, was utilized for the entire described studies. The "UGB" isolate was cultured in a glass bottle containing an under layer of 1% solid agarose (Aneresco, Solon, Ohio) in water with an over layer of 3.5% Czapek-Dox broth (Difco, Becton Dickenson, Sparks, Md.). Cultures were incubated at 37° C. in ambient air. Supernatant of the cultures were harvested when confluent growth of *aspergillus flavus* was achieved, usually on an every two week basis. The supernatant was filtered in a 0.25 μm filter (Corning Inc, Corning, N.Y.) and stored in a refrigerator at 4° C. until used.

EBV type 2 Burkitt's lymphoma Jijoye cell line (CCL-87) and owl monkey B-lymphoblast cell line (CRL-2312) clone 13C (EBV transformed) were obtained from the American Type Culture Collection (ATCC, Manassas, Va.) and cultured according to standard tissue culture protocols and sterile techniques. CCL-87 and CRL-2312 cells were cultured in RPMI 1640 medium (GIBCO Laboratories) supplemented with 10% Fetal Bovine serum (Atlanta Biologicals), 10 mM HEPES (GIBCO Laboratories) and 1 mM Sodium Pyruvate (Sigma-Aldrich). Supernatant from these cell lines that were grown to confluence were used for experiments. CRL-2312 cell lines supernatant was used as negative control.

*Mycocladus corymbifera* species was randomly cultured from normal environmental sources (strawberries), cultured identically to what is described for *aspergillus flavus*, harvested, and supernatant filtered and kept in an identical fashion.

Aflatoxin B1 was obtained from commercial sources (Sigma Chemicals, St. Louis, Mo.) and used as controls.

Aliquots of the *aspergillus flavus*, EBV-infected CCL-87 culture supernatant, and purified Epstein-Barr virus were analyzed by Fast Protein Liquid Chromatography (FPLC). Protein fractions of *aspergillus flavus* (X), Epstein-Barr virus (EBV, eV) and supernatant of their combination, were obtained using an FPLC system (Bio-Rad Laboratories, Inc., Hercules, Calif.) with BioScale™ Macro-Prep Column High Q cartridge. The BioLogic™ LP system was operated along with the following accessories: BioLogic™ LP Controller Gradient Mixer, MV-6 Manual Inject Valve, BioLogic™ LP Optics Module Conductivity Flow Cell in Conductivity Holder, Diverter/Bypass Valves SV-5 buffer-select valve, Model EP-1 Econo gradient pump, Econo UV monitor, Model 2110 fraction collector and LP Data View Software. Purification of each peak was achieved using Sephadex columns and standard protein purification techniques.

After two weeks of incubation, supernatant of culture of *aspergillus flavus* (X) show three distinct peaks, seen in FIG. 1(A), whereas EBV at the same time shows a single, broad peak, seen in FIG. 1(B). Incubating the *aspergillus flavus* (X) with EBV generates a new peak starting after four hours of incubation, seen in FIG. 1(C). A superimposed graph, seen in FIG. 1(D), better demonstrates development of this peak (shown with black squares). The protein fraction shown by this peak is active in the transformation of susceptible cells to cells with leukemic phenotype. This technique can detect individuals with leukemia in remission/long-term survivors. It is of interest that the first peak fraction falls in the same area, i.e. 50-75 KD, as that of Epstein-Barr virus, as evidenced by FIGS. 1(A), (C), and (D). The effects of incubation persist through at least day 7, as evidenced by the similarity in the results taken at 4 hours and 7 days, seen in FIG. 2(A)-(D). However, the signal generated by the fraction at the first peak of the supernatant of culture of *aspergillus flavus* was much larger and broader, seen in FIG. 2(A), and carried over to the extracts co-incubated with EBV, seen in FIG. 2(C). Thus, the incubation of supernatant of culture of *aspergillus flavus* and EBV results in a new peak which was not previously present in the supernatant of culture of *aspergillus flavus* or incubation of EBV alone.

Irradiation of the fractions of supernatant (50 cGy) of the *aspergillus flavus* caused a subtle shift in the fraction's elution point, and reduced the signal of peaks 2 and 3, seen in FIG. 3(A). This effect was not observed with the X+EBV culture, seen in FIG. 3(B). The shift in supernatant of culture of *aspergillus flavus* is especially evident when superimposed on the EBV and evidences an apparent new peak which has, in further studies, increased activity in transformation of susceptible cells to cells with leukemic surface markers and detection of individuals with a history of leukemia.

For studies involving incubation of a combination of different leukemia-inducing substances, the unfiltered supernatants of *aspergillus flavus* cultures were utilized. Twenty five milliliters of this supernatant were co-incubated in 100 ml culture flasks (Sarsted, Inc., Newton, N.C.) with 2 ml of either isolated EBV containing $2\times10^6$ PFU virus or supernatant of CCL-87 cultures. Cultures were incubated at 37° C. with 5% $CO_2$ for 7 days. Cultures were agitated on a daily basis during incubation and filtered in a 2.5 μm filter (Corning Inc, Corning, N.Y.) and kept refrigerated at 4° C. until used.

Example 2

Subject to parental/patient consent, approximately 15 ml of blood was obtained from leukemic patients in remission, long-term survivors of leukemia and normal volunteers. Additional "normal" control samples were collected from the first drawing of blood in sickle cell patients undergoing manual partial exchange transfusion, or samples of blood discarded by the blood bank from normal donors. Patient blood was placed into heparin (1000 USP u/ml). Peripheral blood mononuclear cells (PBMC) were isolated by density gradient centrifugation (400×g, 40 minutes, and 18° C.) with Ficoll Paque Plus (GE Healthcare, Amersham Biosciences; Uppsala, Sweden), followed by washing with phosphate-buffered saline. Plasma was also collected simultaneously and stored at −80° C. until use. Density gradient-isolated PBMC were resuspended in ice-cold fetal bovine serum with 10% dimethyl sulfoxide (DMSO) at $10^7$ cells/ml. Aliquots of cell suspension (1.0 ml) were made in cryovials and immediately transferred to a pre-cooled (4° C.) Nalgene Cryo 1° C. freezing container (Nalge Nunc International, Rochester, N.Y.) and placed in a −70° C. freezer overnight. Frozen specimens were transferred to a liquid nitrogen freezer within 24 hours. Specimens were maintained in liquid nitrogen until thawed and assayed.

Frozen specimens were thawed in a 37° C. water bath with continuous agitation. Each 1 ml of thawed cell suspension was slowly diluted with RPMI 1640 medium (Gibco Laboratories, Grand Island, N.Y.) supplemented with 10% Fetal Bovine serum (Atlanta Biologicals, Norcross, Ga.), 10 mM HEPES (Gibco Laboratories) and 1 mM Sodium Pyruvate (Sigma-Aldrich, St. Louis, Mo.) at room temperature. Cells were centrifuged, and washed twice with 10 ml of medium. These cells (frozen/thawed PBMC) were then assessed for viability by trypan blue dye exclusion, counted, and re-suspended in the medium for assay.

Epstein-Barr virus, aflatoxin and CCL-87 cultures were obtained from commercial sources, and maintained as discussed above. Several controls were utilized, including supernatant of culture of *mycocladus corymbifera* species which was randomly cultured from normal environmental sources (strawberries) and filtered, identical to that described for *aspergillus flavus*. Other controls included avian leukosis virus, aflatoxin and supernatant of owl monkey 1C3 B-lymphoblast cell line (CRL-2312). Standard methodologies for all cultures, flow cytometry, ELISA techniques, FPLC, gel electrophoresis and protein determination were used. Radiation dose, when used, was 50 centiGray.

Control and test patient cells isolated by density gradient were subject to various treatments in vitro. About $1×10^6$ cells were incubated with supernatant of *aspergillus flavus* cultures, CCL-87 supernatant (containing EBV genome) or patients' plasma (from whom the cells were derived) or with various combinations of CCL-87 supernatant+plasma; X+CCL-87 supernatant; supernatant of *aspergillus flavus* cultures+plasma or supernatant of *mycocladus corymbifera* cultures; CCL-87 supernatant+plasma all in the ratio of 1:1 and made up to 10 ml with complete RPMI 1640 medium in 25 cm² cm tissue culture flasks. Cell samples were also exposed to aflatoxin or avian leukosis virus or to CRL-2312 supernatant that served as positive and negative controls. The different treatment flasks were incubated for 4 days at 37° C. and 5% $CO_2$.

At time intervals of 24, 48, 72 and 96 hrs, cell surface phenotyping was performed by flow cytometry. Briefly, cell suspension from each treatment was centrifuged and cell pellets were incubated with anti-CD34-FITC (clone 581, BD Biosciences, Oxford, UK), anti-CD10-PE (clone HI10A, BD Biosciences), anti-CD19-APC (clone HIB19, BD Biosciences), anti-CD45-APC-Cy7 (clone 2D1, BD Biosciences) and anti CD-1,7-PerCP-Cy5.5 (clone 104D2, BD Biosciences) for 45 minutes at 4° C. Cells were washed and re-suspended in stain buffer (BSA, BD Biosciences). Acquisition and Analysis was carried out on fluorescence activated cell sorting (FACS) BD FACS Canto II using FACSDiva v 6.1.2. Samples were gated on the basis of forward- and side-scatter. Dead cells were excluded by setting appropriate threshold values. Percentage of cells positive for CD10CD19, CD34CD19 and CD34CD117 were recorded.

Figure 4:
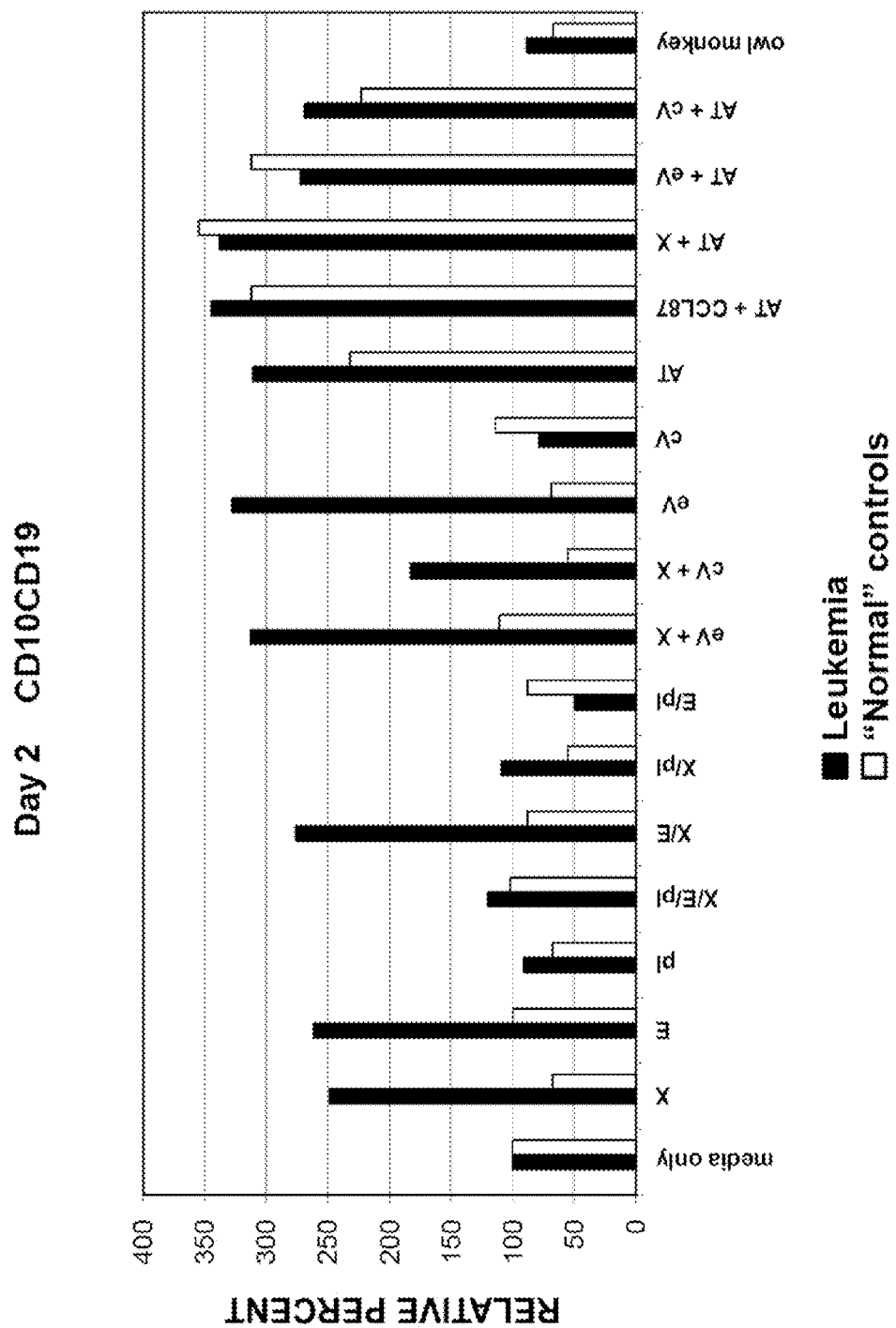
FIG. 4 is a graph showing an example of the relative percentage of cells stained for one of the leukemic (ALL) cell surface markers CD10/CD19 at day 2 of incubation. X is the supernatant of the *aspergillus flavus* fungal culture; E is the supernatant from EBV-infected CCL-87 culture; pl is human plasma; eV is Epstein-Barr-Virus used alone ($2 \times 10^6$ PFU); cV is avian leukosis virus at $2 \times 10^6$ PFU/ml; AT is aflatoxin; OM is owl monkey cell culture supernatant. Mononuclear leukocytes were obtained from a group of long-term survivors of acute lymphoblastic leukemia (ALL) and compared to "normal" controls. Controls were mononuclear cells from a group of sickle cell patients undergoing routine partial exchange transfusions (discarded blood). Cell surface phenotypes (CD 10/19, CD 34/19, CD 34/CD117) were examined daily for four days using a flow cytometer (BD FACS Canto I, Becton, Dickinson, & Co., Franklin Lakes, N.J.). Results of all cell surface markers were similar, thus the results of CD10/19 are shown. These results are expressed as percent of control (for more detailed and standard deviations see FIG. 15).

The results of incubation of blood mononuclear cells from normal subjects, "normal" controls such as sickle cell patients, long-term disease-free survivors of acute lymphoblastic leukemia (ALL cells, called leukemic patients), and non-leukemia cancer patients (cancer patients), were examined for cell surface markers, thereby indicating the leukemic status of the cells, as shown in FIG. 4. As compared to media only, which was used as control, when cells from either leukemic patients in remission on chemotherapy or long-term survivors of leukemia were exposed to the supernatant of *aspergillus flavus* cultures, CCL-87 containing EBV or purified EBV culture, there was a significant increase in cell surface markers, as depicted in FIGS. 4 and 15. The results show that supernatant of *aspergillus flavus*, EBV/EBV containing cultures, and the combination of *aspergillus flavus* and EBV, selectively induce leukemic cell surface markers in leukemic patients and not controls. Other substances used have no differentiating effect. Aflatoxin indiscriminately stimulates cell surface markers in leukemics and controls.

Figure 5:
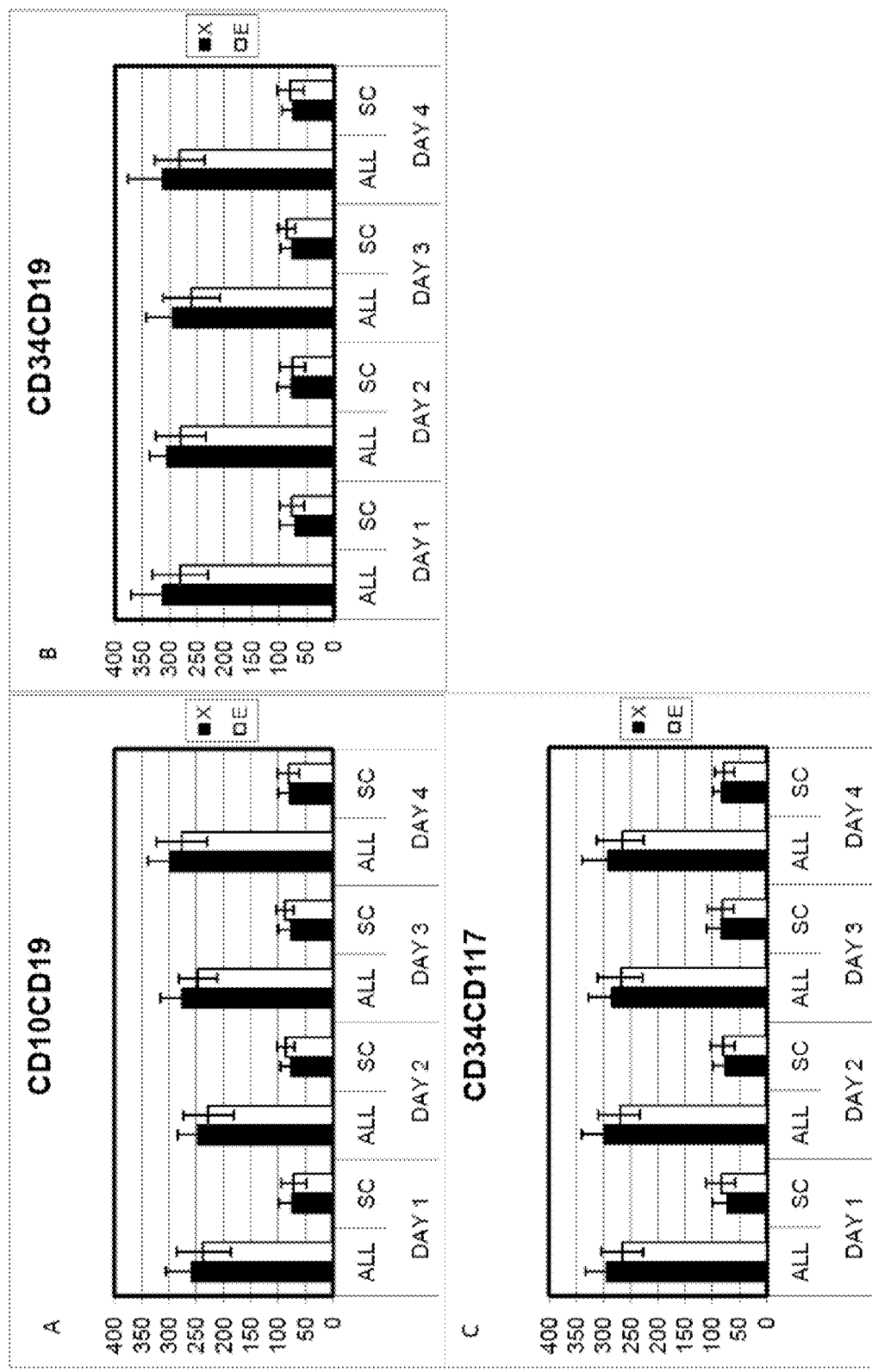
FIGS. 5(A)-(C) are graphs showing cell surface phenotype of mononuclear leukocytes upon exposure to supernatant of *aspergillus flavus* culture or EBV. Cells from long term leukemia survivor patients (ALL) and "normal"/sickle cell patients (SC) (controls) were incubated with either the supernatant of the *aspergillus flavus* fungal culture (X) or the supernatant from EBV-infected CCL-87 culture (E) and detected at days 1-4 post-incubation.
Figure 8:
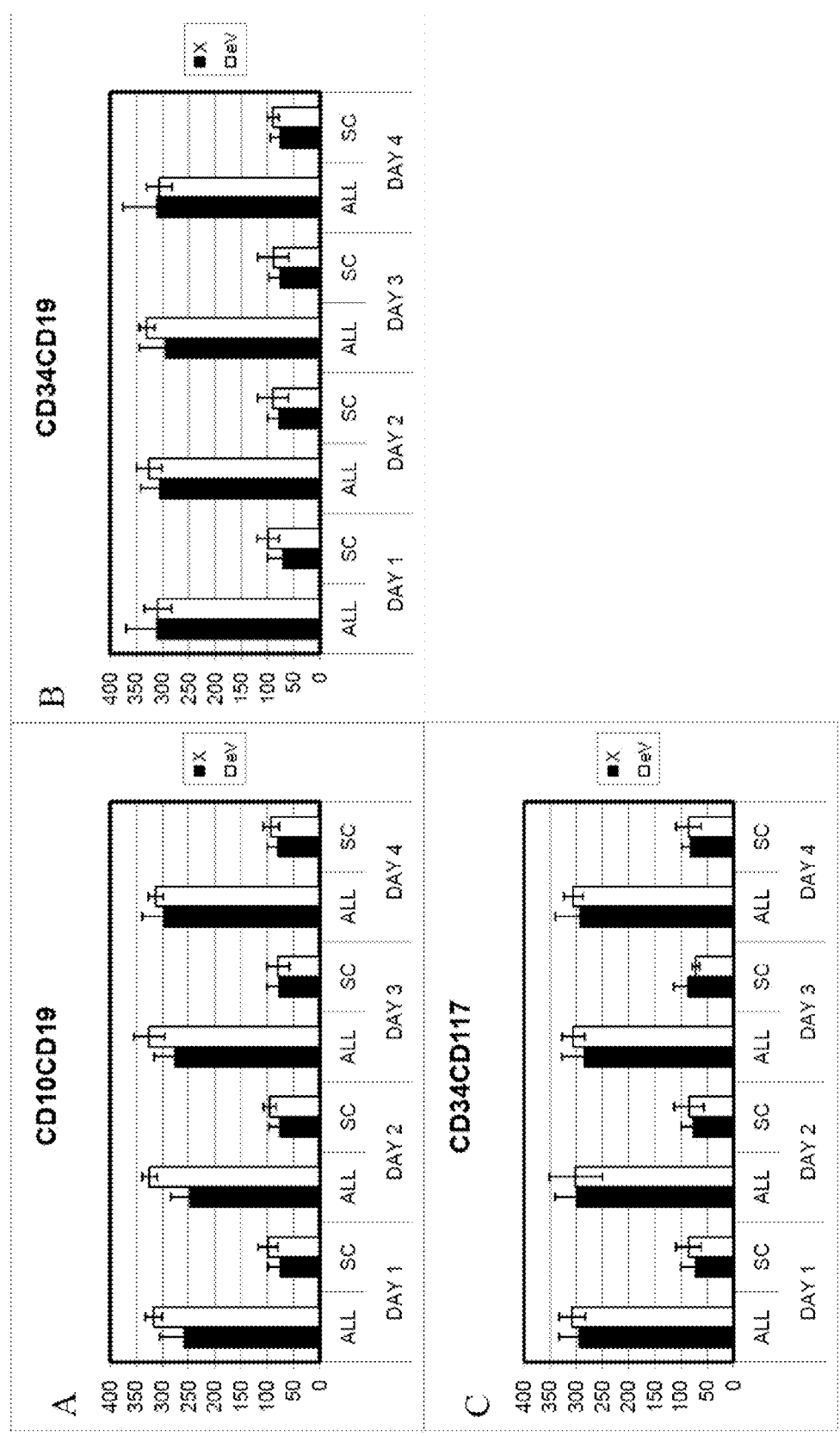
FIGS. 8(A)-(C) are graphs showing cell surface phenotyping of cells from individuals who are long term survivors of leukemia (ALL) exposed to supernatant of *aspergillus flavus* culture (X) as opposed to purified Epstein-Barr Virus (eV) as compared to "normal" sickle cell (SC) controls. The study is repeated daily from day 1-4 post-incubation.
Figure 9:
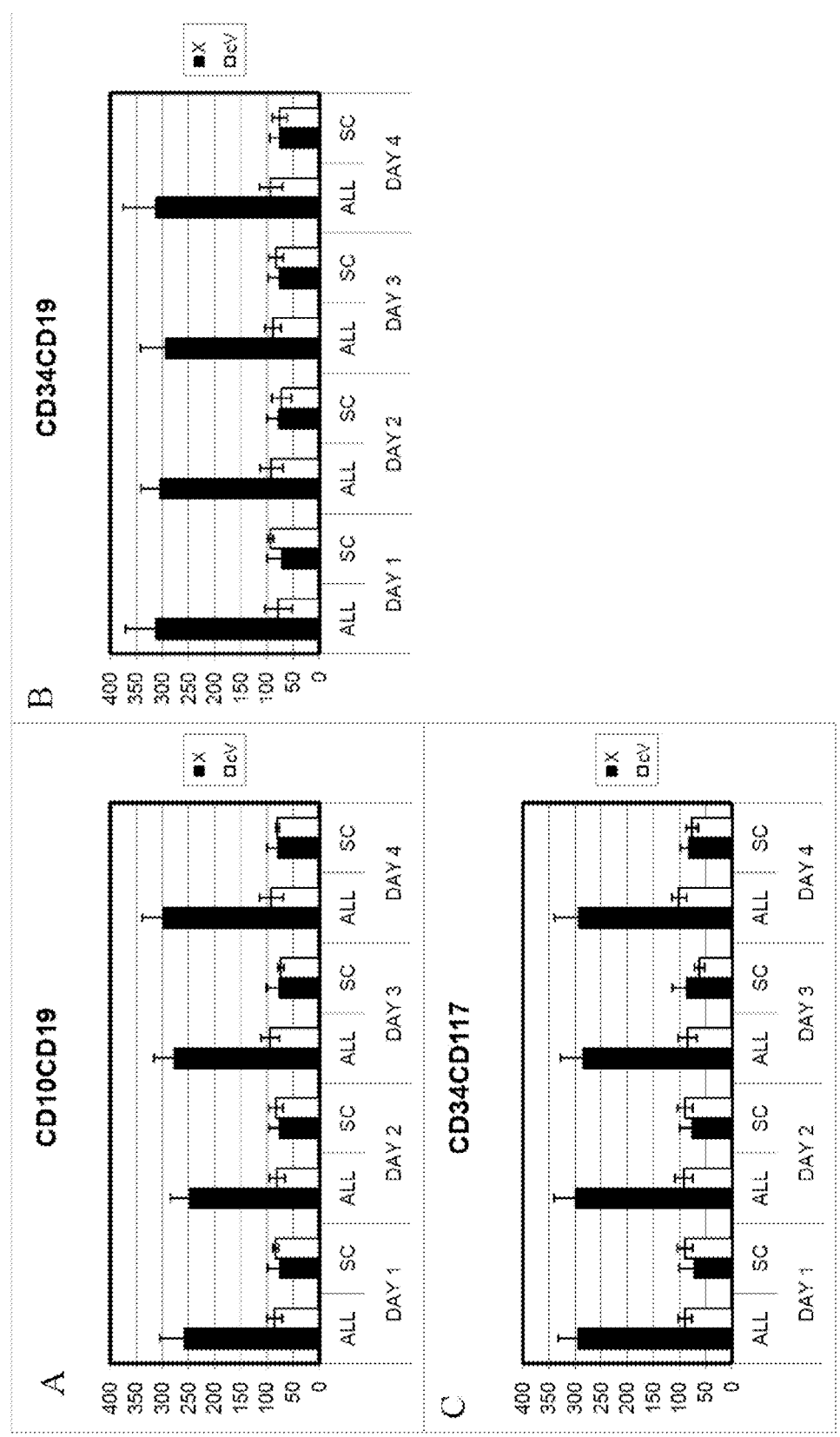
FIGS. 9(A)-(C) are graphs showing cell surface phenotyping of cells from individuals who are long term survivors of leukemia (ALL) exposed to supernatant of *aspergillus flavus* culture (X) as compared to avian leukosis virus (cV). The cultures are evaluated daily from day 1-4 post-incubation. Controls are mononuclear cells from "normal"/sickle-cell (SC) patients.
Figure 11:
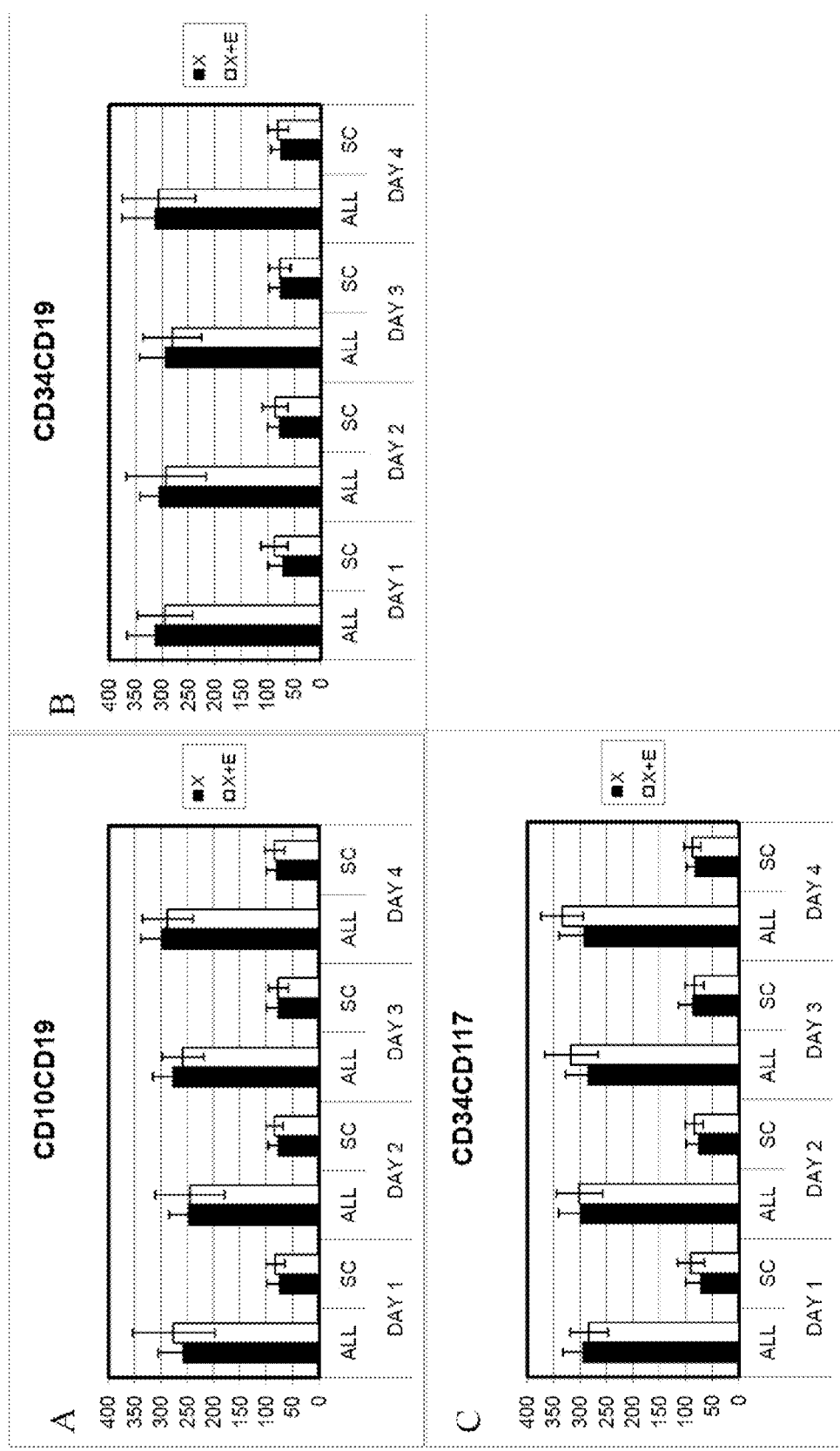
FIGS. 11(A)-(C) are graphs showing cellular phenotyping of cells from individuals who are long term survivors of leukemia (ALL) exposed to supernatant of *aspergillus flavus* culture (X) as compared to a combination of *aspergillus flavus* (X) and Epstein-Barr Virus (emitted from CCL87 cell culture) (E) (X+E). The cultures are evaluated daily from day 1-4 post-incubation. Controls are mononuclear cells from "normal"/sickle cell (SC) patients.
Figure 21:
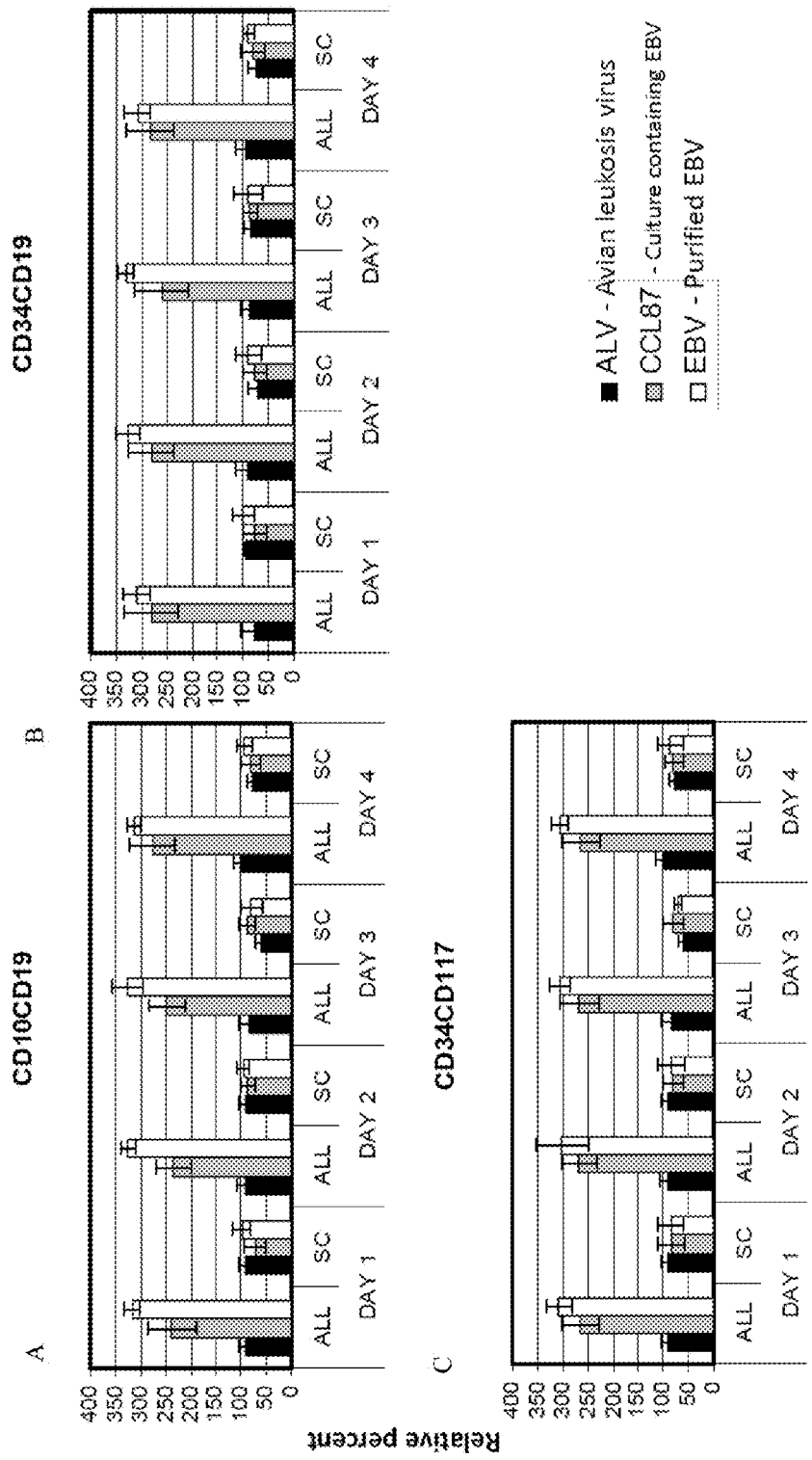
Figure 22:
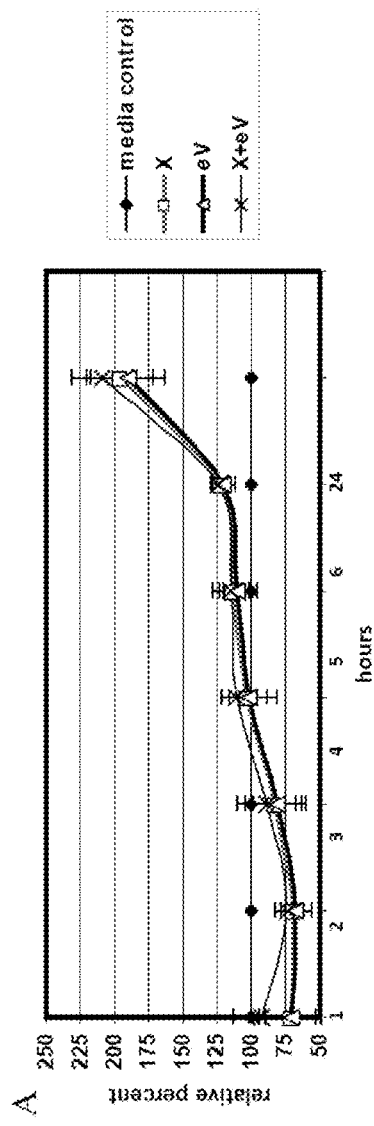
Figure 22:
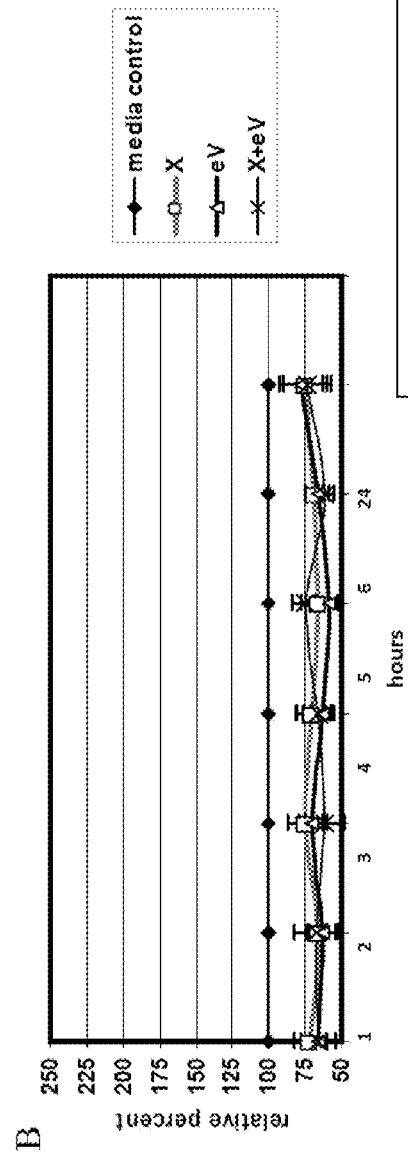
Figure 23:
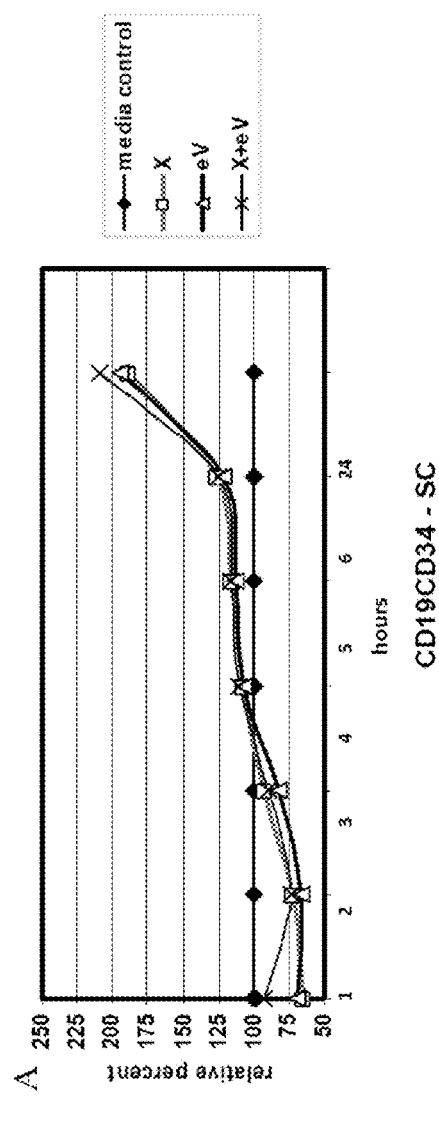
Figure 23:
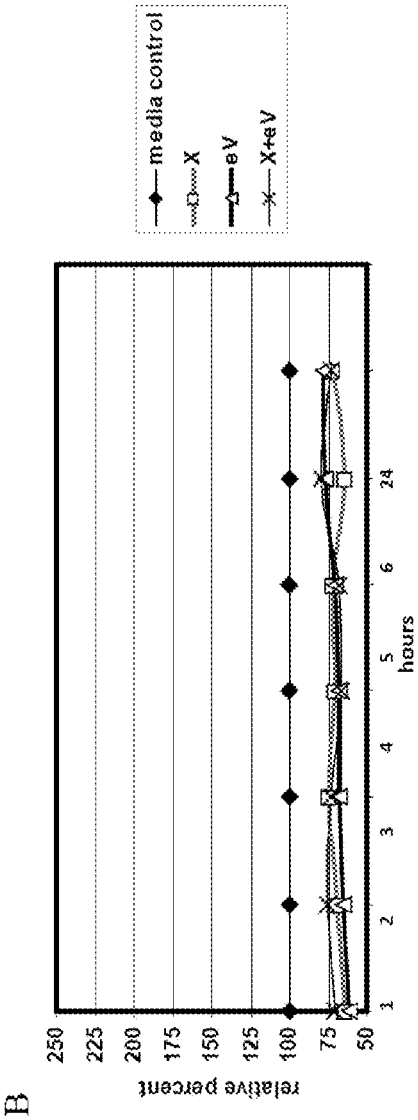

The effects of the inducing substances, such as the *aspergillus flavus* supernatant and EBV, on mononuclear leukocytes from leukemic patients began after four hours of incubation and were fully evident after day 1, as seen in FIGS. 21-23, and persisted beyond that day. The effect of *aspergillus flavus* was evident in samples detected for CD10/CD19, CD34/CD19 and CD34/CD117 combinations. The addition of *aspergillus flavus* or *aspergillus flavus* and Epstein-Barr virus containing CCL-87 stimulates development of cell surface phenotypes characteristic of acute lymphoblastic leukemia in former leukemic patients and not controls, seen in FIGS. 11(A)-(C) or with purified Epstein-Barr virus, seen in FIGS. 8(A)-(C). Supernatant of cultures of *aspergillus flavus* and Epstein-Barr Virus (eV) showed an equivalent effect on development of cell surface phenotyping for leukemia-predisposed individuals, and showed no effect on cells from sickle cell patients (normal controls). Similar responses, as seen in the leukemic patients were not observed in "normal" controls, as seen in FIGS. 5(A)-(C). Further, the cells taken from long-term survivors of leukemia can be re-induced to develop cell surface markers characteristic of acute lymphoblastic leukemia (ALL) with supernatant of *aspergillus flavus* with or without Epstein-Barr Virus, FIG. 11(A)-(C). This effect was specific to individuals with leukemia predisposition, as neither *aspergillus flavus* supernatant of culture nor *aspergillus flavus* supernatant of culture with EBV had effects on controls, as seen in FIGS. 15(A)-(C).

Figure 6:
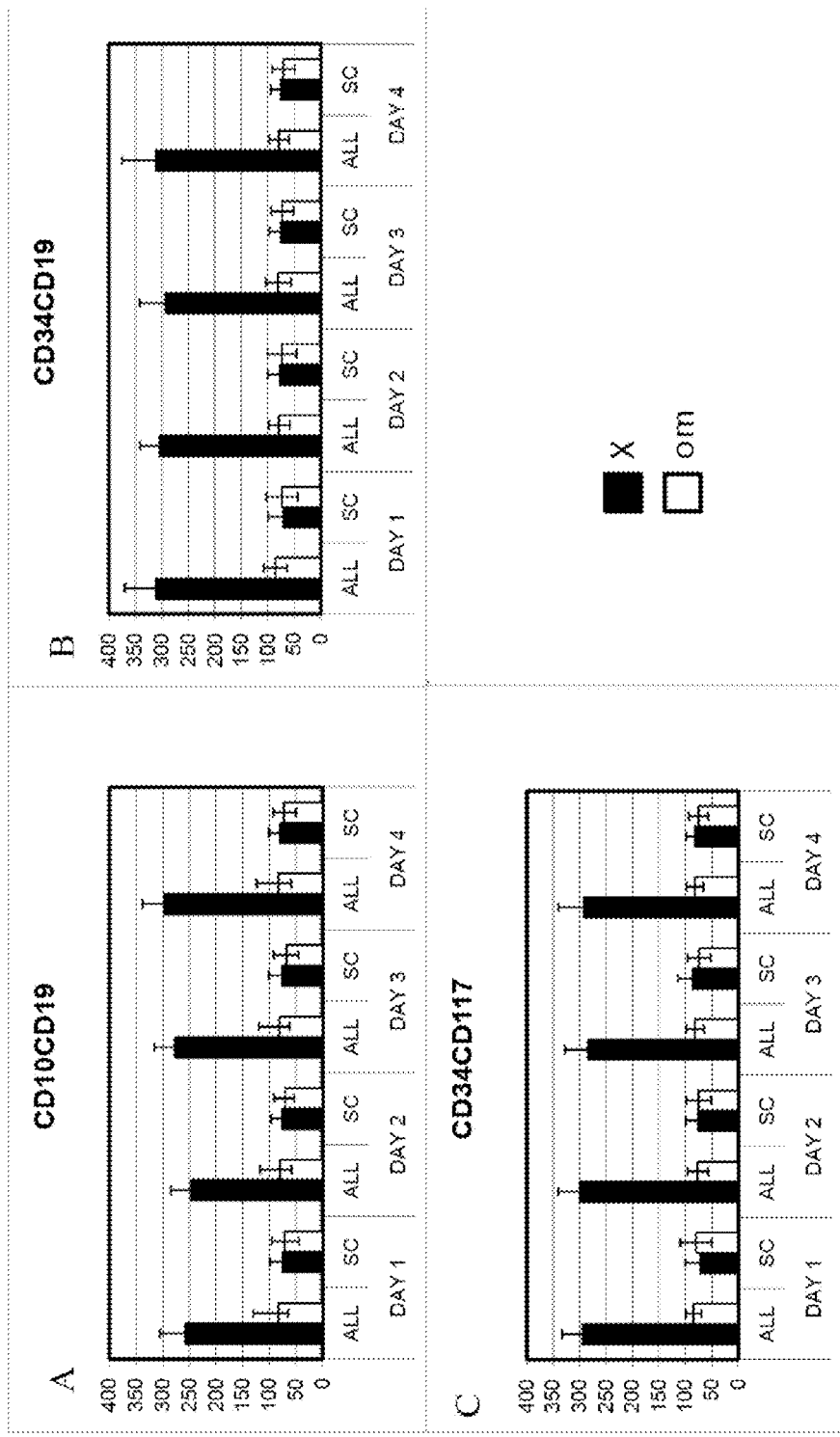
FIGS. 6(A)-(C) are graphs showing cell surface phenotypes. Cells from former leukemic patients (ALL) and "normal"/sickle cell samples (SC) (controls) were incubated with either the supernatant of the *aspergillus flavus* fungal culture filtered through 2.5 μm filter (Corning Inc, Corning, N.Y.) (X) or owl monkey cell culture supernatant (CRL-2312) (om) and cell surface phenotypes were examined at days 1-4 post-incubation. Cell surface phenotypes characteristic of acute lymphoblastic leukemia (ALL) were evaluated daily for four days after incubation using a flow cytometer (BD FACS Canto II, Becton, Dickinson, & Co., Franklin Lakes, N.J.). Results are expressed as percentage of control.
Figure 7:
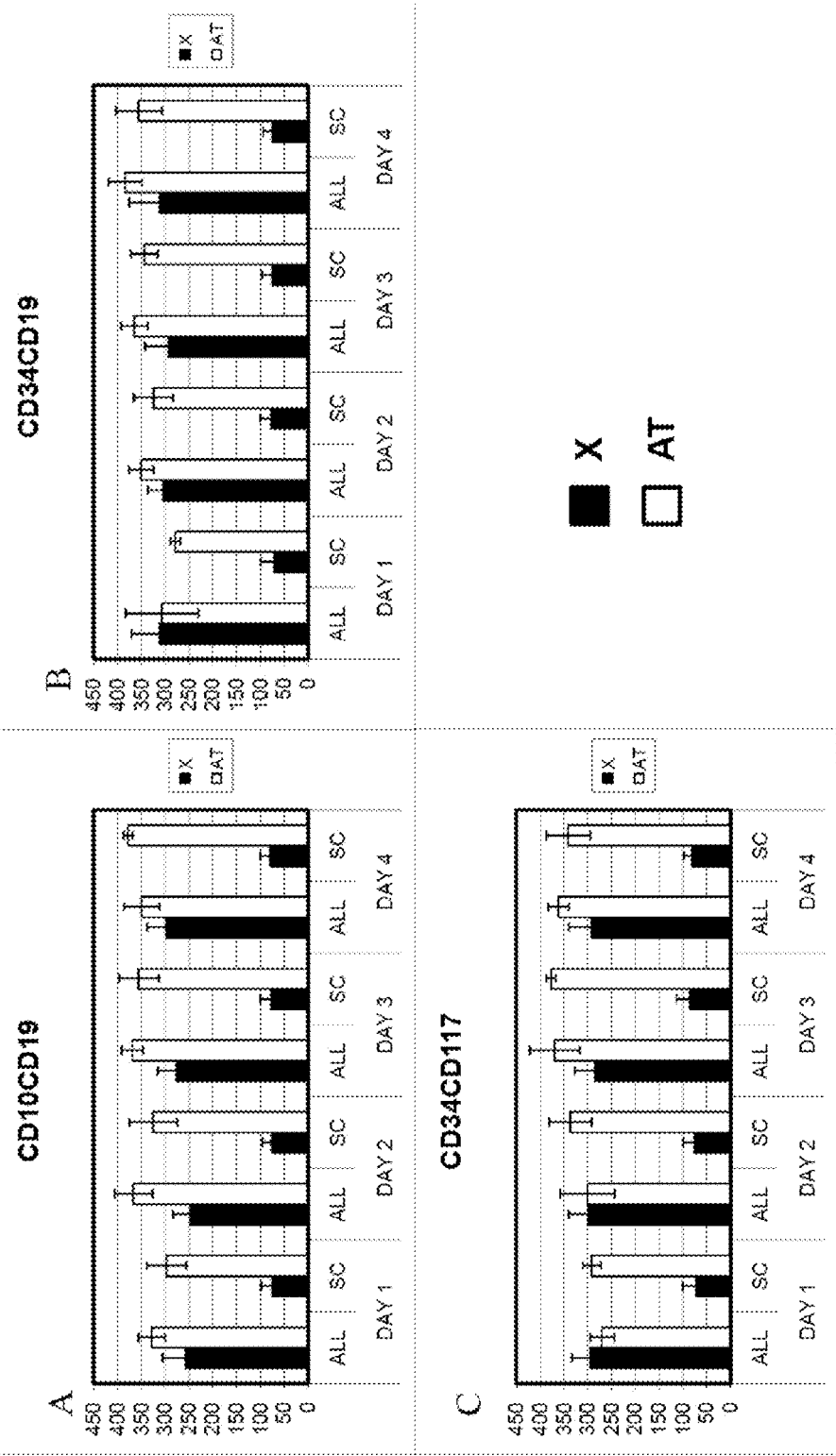
FIGS. 7(A)-(C) are graphs showing cell surface phenotyping. Mononuclear cells from long-term survivors of leukemia patients (ALL) and "normal"/sickle cell samples (SC) (controls) were incubated with either the supernatant of the *aspergillus flavus* fungal culture (X), or 10 ng/ml aflatoxin B1 (AT), and compared to "normal" controls. The cultures were evaluated and detected at days 1-4 post-incubation.
Figure 10:
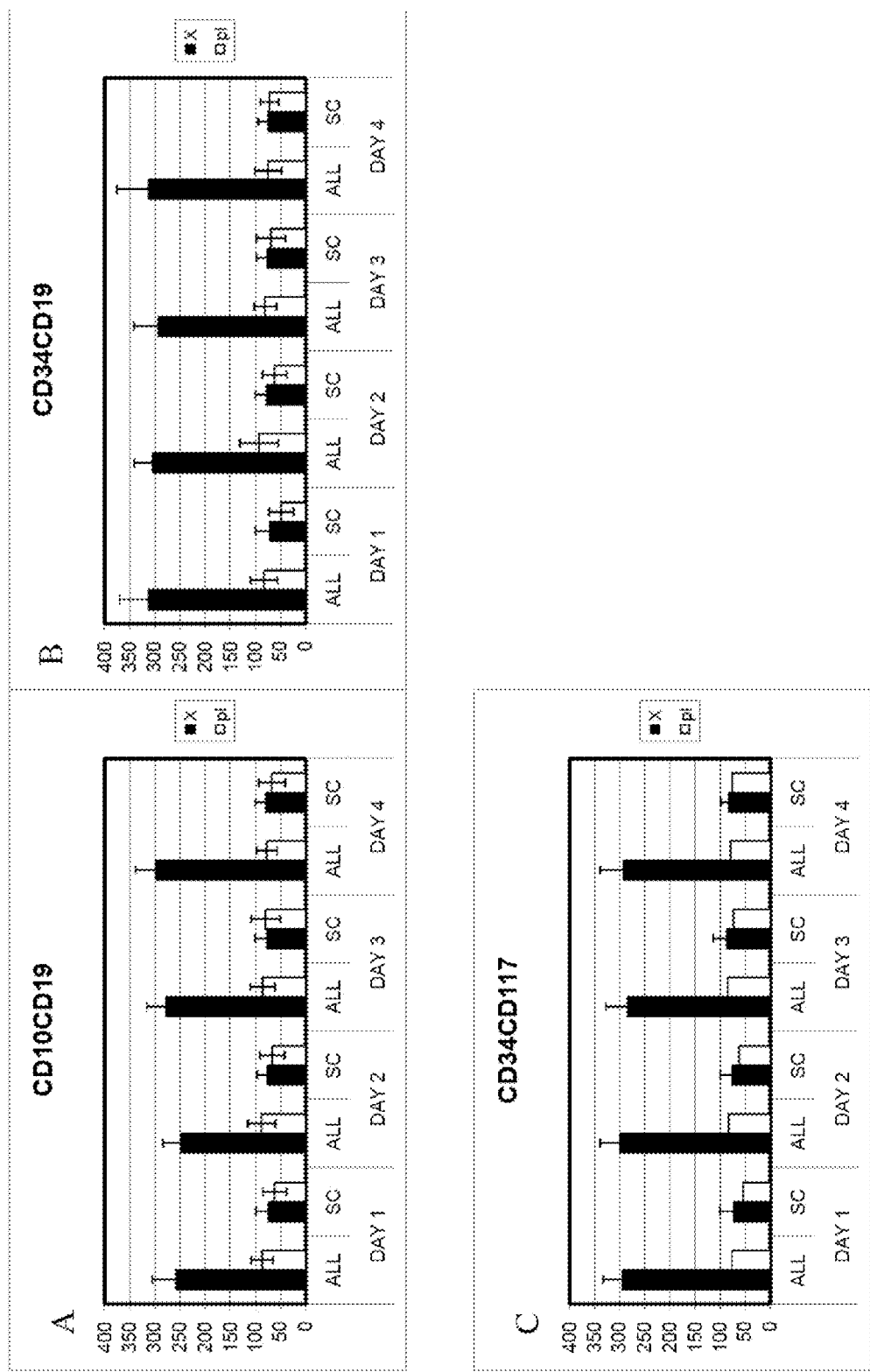
FIGS. 10(A)-(C) are graphs showing cellular phenotyping of cells from individuals who are long term survivors of leukemia (ALL) exposed to supernatant of *aspergillus flavus* culture (X) as compared to autologous plasma (pl). The cultures are evaluated daily from day 1-4 post-incubation.

Notably, this selective effect on cell surface markers was specific to former leukemic patient samples by the induction of leukemic cell surface phenotypes. Such a discriminating effect in re-induction of leukemic cell surface markers heretofore has neither been known to occur nor reported. Further, cell incubation with other compounds, such as owl monkey 1C3 B-lymphoblast cell line (CRL-2312) cell culture supernatant, seen in FIGS. 6(A)-(C), avian leukosis virus, seen in FIGS. 9(A)-(C) and FIGS. 12(A)-(C), and human plasma, seen in FIGS. 10(A)-(C), did not increase cell surface markers in any of the samples. In contrast to supernatant of *aspergillus flavus* cultures or EBV, cell incubation with purified aflatoxin (AT) indiscriminately induced increased development of CD10/CD19, CD 34/CD19 and CD34/CD117 in both normal and leukemic cells, as seen in FIGS. 7(A)-(C). The addition of plasma to the mixture reduced, but did not eliminate this effect, FIGS. 10 (A)-(C) and 15 (A)-(C).

Further, the combination of CCL-87 or EBV, with the supernatant of *aspergillus flavus*, resulted in the development of the above cell surface phenotypes as percent of control, regardless of whether the cells were incubated with CCL-87/*aspergillus flavus* or purified EBV/*aspergillus flavus*, as seen in FIG. 15(A)-(C). The effect was consistent in all acute lymphoblastic leukemias, and within diffuse lymphoma patients. However, the combination of CCL-87/*aspergillus flavus* or EBV/*aspergillus flavus* had no effect on cell surface phenotype of "normal" controls or patients with solid tumors, which mirrors the results from exposing "normal" cells to EBV or supernatant of *aspergillus flavus* alone. *Mycocladus corymbifera* was compared to the supernatant of culture of *aspergillus flavus* to establish if all fungal agents can induce similar effects in the aforementioned leukemic population, with aflatoxin (AT) used as an indiscriminate positive control. The supernatant of *aspergillus flavus* (X) used in this study discriminated between former leukemic patients and controls with the development of cell surface phenotyping, thus correctly identifying former leukemic patients. By comparison, *mycocladus corymbifera* (MC) did not identify or discriminate between former leukemic patients and "normal"/sickle cell controls, showing that this effect, within our experiment, is specific to the *aspergillus flavus* supernatant of culture, as seen in FIGS. 14(A)-(C).

A summary of the results is seen in FIGS. 15(A)-(C), showing that incubation of *aspergillus flavus*, EBV-infected CCL-87 culture supernatant, purified Epstein-Barr virus, and combinations of *aspergillus flavus* with EBV-infected CCL-87 culture supernatant or *aspergillus flavus* with purified Epstein-Barr virus, selectively increase cell surface markers in former leukemic patients. When purified aflatoxin was added to either supernatant of *aspergillus flavus*, cells from both leukemic and normal individuals exhibited leukemic cell surface phenotypes showing aflatoxin was non-specific, as seen in FIGS. 15(A)-(C). Supernatant of the owl monkey 1C3 B-lymphoblast cell line (CRL-2312) culture, which was used as a non-specific negative control, and human plasma failed to have a significant effect on cell surface phenotype on leukemic or "normal" control cells, as seen in FIGS. 15(A)-(C). Thus, within our experiment, only supernatant of the culture of *aspergillus flavus* (X) and EBV-containing cultures (E and eV) stimulate development of cell surface phenotype characteristic of acute lymphoblastic leukemia (ALL) in former leukemic patients and not controls. Others such as a viral agent e.g. avian leukosis virus, plasma or a fungal agent such as *mycocladus corymbifera* (cV, pl, (MC), respectively) do not stimulate development of any cell surface phenotype in leukemics and controls and AT stimulates development of such surface markers on all cells indiscriminately including cells from former leukemics and controls.

Effects of radiation: When cultures of *aspergillus flavus* alone or incubated with EBV, as described above, were irradiated with 50 CentiGray of radiation, supernatant of the latter culture showed an increase in activity for induction of leukemic phenotypes in cells from leukemia patients in remission, as determined by flow cytometry, but did not induce any leukemic phenotypes in normal controls. This may indicate radiation can provoke induction of leukemia-inducing proteins by these organisms.

Data are presented as the arithmetic mean±standard deviation (SD). Results were analyzed using a two-tailed Student's t-test to assess statistical significance. Statistical differences are presented at probability levels of $p<0.05$.

Example 3

For ELISA studies, subject to parental/patient consent, approximately 15 ml of blood was obtained from leukemic patients in remission, long-term survivors of leukemia and normal volunteers. Additional "normal" control samples were collected, subject to consent, from the first drawing of blood in sickle cell patients undergoing manual partial exchange transfusion. Additionally, discarded blood from the blood bank was used as control. Patient blood was placed into heparin (1000 USP u/ml). Plasma was also collected simultaneously and stored at −80° C. until used.

A qualitative sandwich ELISA was performed to detect antibodies in plasma samples against antigens in various conditioned media. Briefly, 96 well microtiter plates were coated with 100 μl of either media, XRT, CCL-87 supernatant or CRL-2312 supernatant or a combination of XRT and CCL-87 supernatant and incubated overnight at 4° C. Plates were then blocked with 2% BSA in PBS for 2 hours at 37° C. Serum samples (100 μl) were loaded in triplicates and incubated for 2 hours at room temperature. Finally, goat anti-human IgG conjugated with Alkaline Phosphatase (Promega, Madison, Wis.) was diluted 1:5000 in blocking buffer and added (100 μl) to each well. Plates were incubated for an additional 2 hours at room temperature and the reaction was visualized by the addition of 50 μl of chromogenic substrate (PNPP, Thermo Fisher Scientific, Lafayette, Colo.) for 30 minutes. The reaction was stopped with 100 μl $H_2SO_4$ and absorbance at 450 nm was measured with reduction at 630 nm using ELISA plate reader. Plates were washed five times with washing buffer (PBS, pH 7.4, containing 0.1% (v/v) Tween 20) after each step.

In quantitative ELISA testing, there was a significant difference when supernatant of *aspergillus flavus* was tested against plasma of patients with ALL, normal controls or non leukemic cancer patients (solid tumors). With ELISA technique, using supernatant of culture of *aspergillus flavus*, or culture of CCL-87 containing EBV, or a combination, it was possible to distinguish plasma from leukemia/diffuse lymphoma patients from that of "normal" controls, as seen in FIGS. 16(A), 17(A), and 19(A).

After incubation with *aspergillus flavus* fungal culture, IgG immunoreactivity for leukemic patient increased significantly, forming a grouping distinct from "normal" samples. This allowed plasma from former leukemic patients to be easily distinguished from that of controls including sickle cell (SC) and normal blood donors (discarded blood from blood bank), as seen in FIG. 16(A). This group of leukemic patients did not overlap with the normal samples. Further, incubating the leukemic patient samples with EBV-infected CCL-87 culture or supernatant from *aspergillus flavus* fungal culture and CCL-87 (X+CCL-87), FIG. 19 (D)-(F), resulted in the same grouping of two distinct groups of leukemic patients versus "normal" samples, as seen in FIGS. 17(A) and 19(A). Supernatant of *aspergillus flavus* or CCL-87 culture containing EBV did not recognize or separate plasma from patients with other cancers (i.e. solid tumors), as seen in 16(B) and 17(B). The stratification of leukemic patient samples from non-leukemic samples is dependent upon the induction factor used, as owl monkey 1C3 B-lymphoblast cell line (CRL-2312) cell culture supernatant did not increase the IgG immunoreactivity of the samples, seen in FIGS. 18(A)-(C). Thus, the inventive ELISA test utilizing supernatant of *aspergillus flavus* or EBV or their combination can differentiate plasma from normal individuals from those of leukemics. Similar results were obtained when Epstein-Barr virus containing supernatant of CCL-87, alone or in addition to supernatant of *aspergillus flavus* were tested against normal, ALL or solid tumor patients' plasma (FIGS. 17(A)-(C) and 18 (D)-(F). The fraction exhibiting the first peak of *aspergillus flavus* separated by FPLC was found to be the most effective in separating plasma from former leukemia patients as compared to controls, as seen in FIGS. 20(A) and (B). Peak 2 has much less activity and appeared to overlap the controls, while peak 3 is less active for detection of former leukemia patients versus controls, seen in FIG. 19(A). Incubation of *aspergillus flavus* peak 1 fractions with EBV showed an increased stratification, with a minor increase in activity for peak 2 fractions, and no change in peak 3 fractions, as seen in FIGS. 19(B) and (C). None of the peaks differentiated patients with solid tumors from sickle cell patients or normal individuals.

The source of EBV did not significantly change the induction of cell surface phenotype characteristic of ALL in former leukemia patients, as seen in FIGS. 21(A)-(C). Both EBV sources clearly predict and separate leukemic cells from normal or solid tumor patients.

Data were presented as the arithmetic mean±standard deviation (SD). Results were analyzed using a two-tailed Student's t-test to assess statistical significance. Statistical differences are presented at probability levels of $p<0.05$.

Example 4

The studies described herein reveal that purified mononuclear leukocytes obtained from the peripheral blood of patients with ALL or diffuse lymphoma, currently on therapy and those off treatment, including some who have been treated many years prior to this investigation, react when exposed to supernatant of *aspergillus flavus* culture or EBV sources or combination of the two, by forming blast cells which by cell surface phenotyping are indistinguishable from the leukemia cells. The exposed cells demonstrate cell surface phenotypes that are hallmarks of acute lymphoblastic leukemia and diffuse lymphomas. Such a reaction is enhanced by addition of supernatant of CCL-87 culture containing Epstein-Barr virus (EBV) or addition of purified EBV. Furthermore, irradiation of *aspergillus flavus* to 50 CentiGray resulted in enhanced stimulation. Combined culture of *aspergillus flavus* and EBV combination resulted in production of an additional protein peak, seen in FIGS. 1(C) and 2(C). This protein was highly effective in detection of individuals with a history of acute lymphoblastic leukemia/diffuse lymphomas and not normal samples, using ELISA technique. This substance also induced ALL leukemic phenotypes in mononuclear peripheral blood cells of former leukemia patients, and not the controls.

By ELISA technique, the plasma of the ALL or diffuse lymphoma patients reacted with the supernatant of cultures of *aspergillus flavus*. A clear separation of leukemic and "normal" control could be obtained. Similar results were not obtained when plasma from normal controls or individuals with solid tumors which were treated in vitro in an identical fashion, were used.

Figure 1:
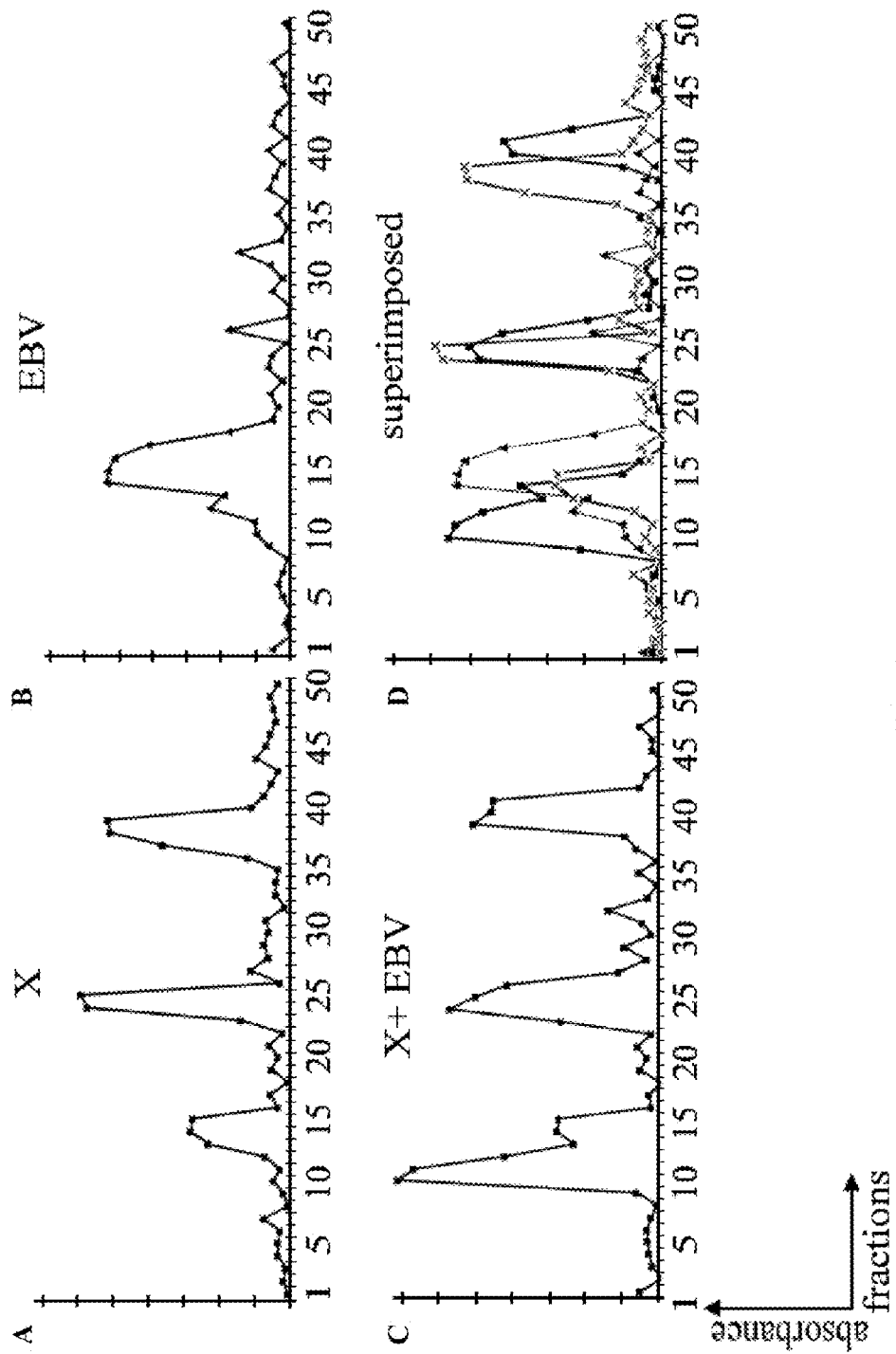
FIG. 1 (A)-(D) is an FPLC analysis of fraction isolates taken from the supernatant of (A) *aspergillus flavus* culture alone (X), (B) purified Epstein-Barr Virus (EBV), (C) the combination of supernatant of cultured *aspergillus flavus* and EBV (X+EBV), and (D) all graphs superimposed.
Figure 2:
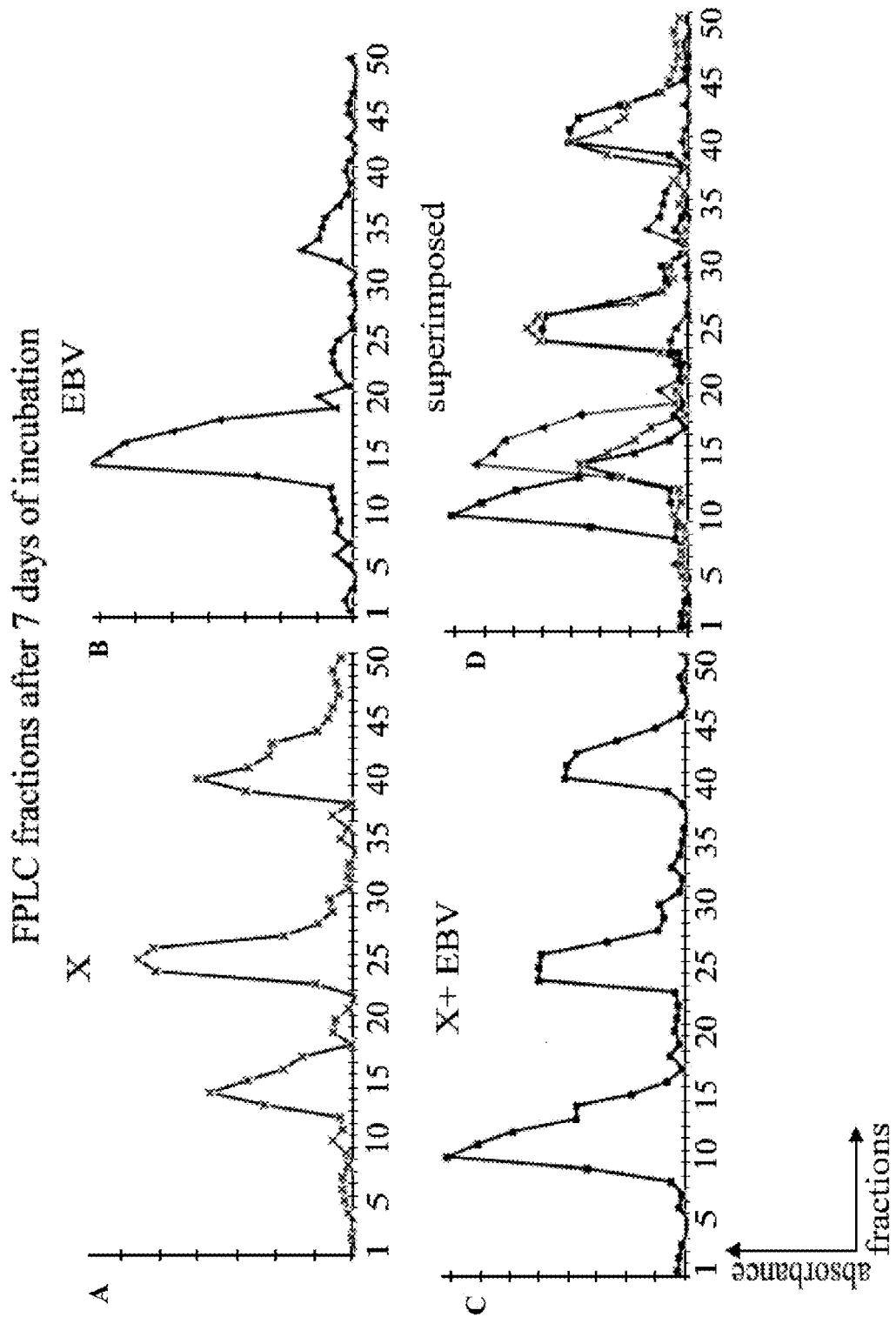
FIG. 2(A)-(D) reveals FPLC fractions of supernatant of culture of (A) *aspergillus flavus* (X), (B) incubated purified Epstein-Barr Virus (EBV), (C) a combination of *aspergillus flavus* and Epstein-Barr Virus (X+EBV) incubated for seven days, and (D) a superimposed graph showing development of the new peak not present in singular incubation of *aspergillus flavus* (X) or Epstein-Barr Virus (EBV).
Figure 3:
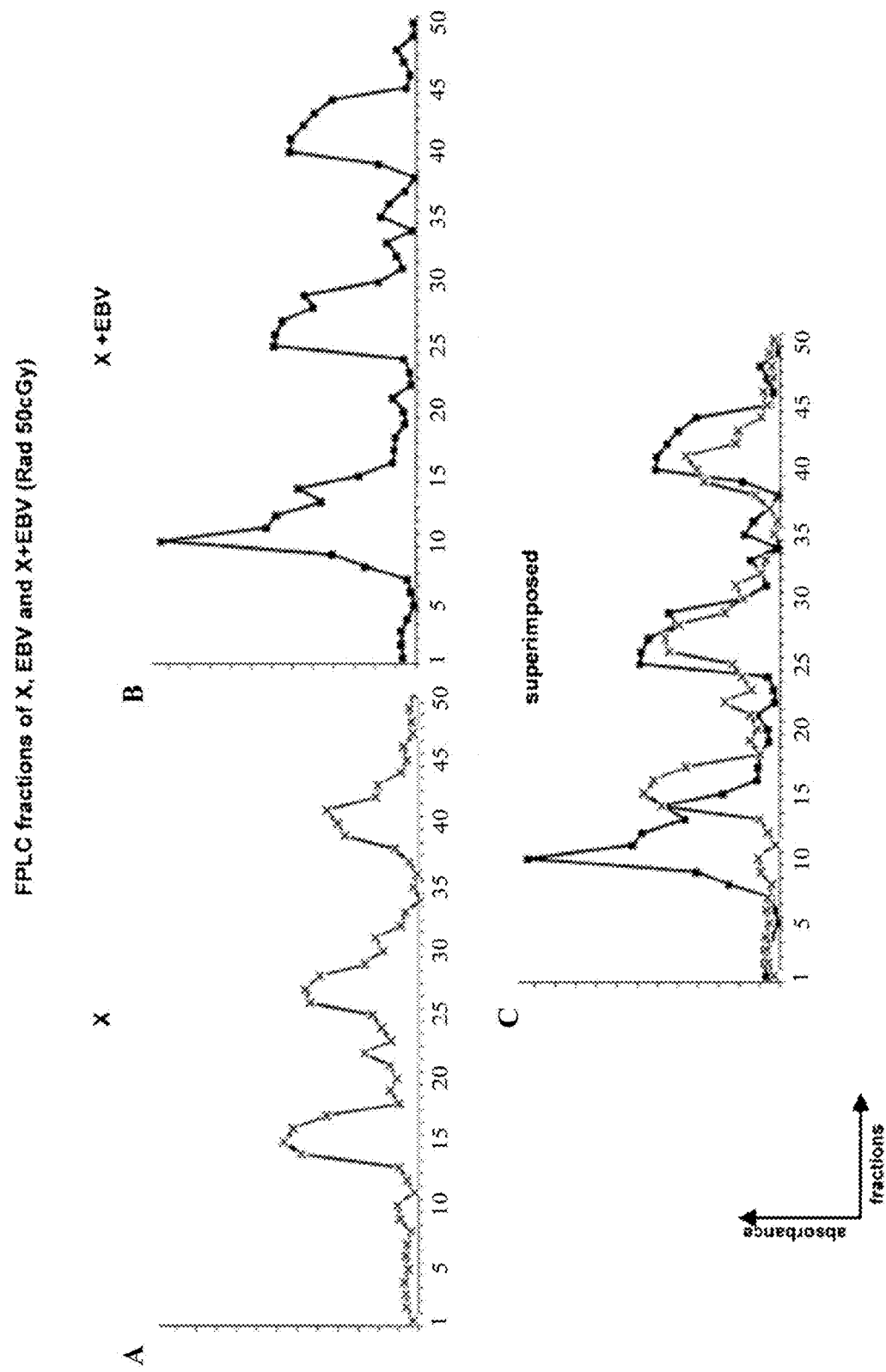
FIG. 3(A)-(C) reveals FPLC fractionation of supernatant of (A) *aspergillus flavus* (X), (B) a combination of *aspergillus flavus* and Epstein-Barr Virus (X+EBV) after 50 centiGray (cGy) of irradiation, and (C) both graphs superimposed.

Radiation of cultures containing *aspergillus flavus* with or without EBV enhanced production of protein peaks, seen in FIGS. 1(A)-(C) versus 3(A)-(C). Further, irrespective of irradiation, peak 1 fractions, with and without incubation, were the most active in the development of CD10/CD19, CD34/CD19, and CD34/CD117 cell surface phenotypes, characteristic of leukemia cells in former leukemic patients, seen in FIGS. 20(A)-(C). Combination of *aspergillus flavus* (X) and Epstein-Barr virus (EBV) with and without irradiation had significant activity, whereas supernatant of owl monkey 1C3 B-lymphoblast cell line (CRL-2312) (OM) had no effect on cell surface phenotypes of former leukemic patients or controls.

A time analysis revealed a gradual development of leukemic cell surface phenotype in former leukemic patients after one, two, three, four, five, six, and 24 hours of incubation with *aspergillus flavus* (X), Epstein-Barr Virus (eV), or a combination of X and eV, as compared to control (media only). Furthermore, the analysis indicates that the cells reduce their expression of cell surface markers within the first 3 hours of incubation with *aspergillus flavus* (X), Epstein-Barr Virus (eV), or a combination of X and eV, as seen in FIGS. 22(A), 23(A), and 24(A). At 4 hours, the cells exhibit about the same signaling as media-treated cells and then begin to continually increase surface markers to at least 24 hours. This effect is not observed with cells from "normal"/sickle cell controls, as seen in FIGS. 22(B), 23(B), and 24(B). Without being bound to any specific theory, it is thought that these results evidence an initial resistance of the cells to revert to a leukemic state, followed by the re-induction of leukemic markers in former leukemia patients.

Substitution of the supernatant of culture of *aspergillus flavus* with *mycocladus corymbifera* species or purified commercially available aflatoxin and replacement of EBV with avian leukosis virus, did not result in similar discriminative changes in normal and leukemic/diffuse lymphoma samples. This indicates that the effect of supernatant of *aspergillus flavus* and EBV are unlikely to be due to general, species nonspecific organisms.

The finding that both EBV and supernatant of *aspergillus flavus* re-induce ALL/diffuse lymphoma phenotypic changes on cells from ALL and diffuse lymphoma patients and not "controls", including solid tumor patients, evidences a potential genetic disposition of these individuals. Furthermore, the fact that cells from ALL and diffuse lymphoma patients react similarly is of significance. Clinically, these two groups are clearly related, as diffuse lymphomas can convert to leukemia. Finding similar results using either cell surface phenotyping or ELISA technique is of significance. These studies may shed light on the effects of EBV and *aspergillus* in generation of leukemia in genetically susceptible patients. Furthermore, the fact that radiation alters the pattern of protein production by *aspergillus flavus* alone or after incubation with EBV may shed a new light on the mechanism of carcinogenesis by radiation.

Reactivation of genomes controlling cell surface phenotypes in former leukemic patients heretofore has not been known. The above studies reveal that despite seemingly complete morphological remission, cells from patients with acute lymphoblastic leukemia upon exposure to certain conditions have capability of transformation to cell surface phenotype similar to those of acute lymphoblastic leukemia. Similar exposures do not induce phenotypic changes in normal individuals or those with solid tumors. ELISA testing can be used as a means to detect and separate patients with a prior history of leukemia, post-ex-facto, from normal individuals and those with solid tumors. The test can potentially be utilized for mass screening of normal individuals to detect susceptibility to developing leukemia. Such an effort requires a large population. The results of the above experiments may also have implication for the etiology of leukemia.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of methods of diagnosing and vaccinating individuals for leukemia, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of altering mononuclear cells obtained from a patient, comprising administering a leukemic inducing factor to the mononuclear cells;

wherein the leukemic inducing factor is supernatant from an *Aspergillus* species culture supernatant or protein purified from an *Aspergillus* species supernatant, EBV-infected CCL87 cell culture supernatant, purified EBV culture or combinations thereof;

wherein the mononuclear cells are collected from a patient inflicted with leukemia, a patient being treated for leukemia, or a patient previously treated for leukemia; and wherein the administration of leukemic inducing factor forms blast cells from the mononuclear cells.

2. The method of claim 1, wherein the leukemic inducing factor is supernatant from an *Aspergillus* species culture supernatant or protein purified from an *Aspergillus* species supernatant.

3. The method of claim 1, wherein the blast cells have a surface phenotype homologous to leukemia cells.

* * * * *